(12) United States Patent
Vali et al.

(10) Patent No.: US 10,098,880 B2
(45) Date of Patent: Oct. 16, 2018

(54) COMBINATION OF NELFINAVIR, METFORMIN AND ROSUVASTATIN FOR TREATING CANCER CAUSED BY ABERRATIONS IN PTEN/TP53

(71) Applicant: CELLWORKS GROUP INC., San Jose, CA (US)

(72) Inventors: Shireen Vali, Bangalore (IN); Shahabuddin Usmani, Bangalore (IN); Zeba Sultana, Bangalore (IN); Ansu Kumar, Bangalore (IN); Taher Abbasi, Bangalore (IN); Robinson Vidva, Bangalore (IN)

(73) Assignee: CELL WORKS GROUP INC., San Jose, CA (US)

( * ) Notice: Subject to any disclaimer, the term of this patent is extended or adjusted under 35 U.S.C. 154(b) by 0 days.

(21) Appl. No.: 15/309,144

(22) PCT Filed: May 5, 2015

(86) PCT No.: PCT/IB2015/053269
§ 371 (c)(1),
(2) Date: Nov. 4, 2016

(87) PCT Pub. No.: WO2015/170248
PCT Pub. Date: Nov. 12, 2015

(65) Prior Publication Data
US 2017/0056404 A1     Mar. 2, 2017

(30) Foreign Application Priority Data
May 5, 2014   (IN) .......................... 2255/CHE/2014

(51) Int. Cl.
*A61K 31/505*   (2006.01)
*A61K 31/155*   (2006.01)
*A61K 31/472*   (2006.01)

(52) U.S. Cl.
CPC .......... *A61K 31/505* (2013.01); *A61K 31/155* (2013.01); *A61K 31/472* (2013.01)

(58) Field of Classification Search
CPC ... A61K 31/505; A61K 31/155; A61K 31/472
See application file for complete search history.

(56) References Cited

PUBLICATIONS

Pyrko et al (Cancer Research, 2007, 67(22), 10920-10928).*
Isakovic et al (Cell and Molecular Life Sciences, 2007, 64, 1290-1302).*
Humberto et al (Cancer Chemother Pharmacol, 2011, 67, 1193-1201).*
Busti et al (J. Cardiovasc. Pharmacol., 2008, 51(6), 605-610).*
Zhang et al (Drug Metabolism and Disposition, 2005, 33(11), 1729-1739).*
Hirani et al (Drug Metabolism and Disposition, 2004, 32(12), 1462-1467).*
Pushparaj et al (J. Ethnopharmacology, 2000, 72, 69-76).*
Stalker, T. et al., "A new HMG-CoA reductase inhibitor, rosuvastatin, exerts anti-inflammatory effects on the microvascular endothelium: the role of mevalonic acid," British Journal of Pharmacology, vol. 133, No. 3, Jun. 2001, 7 pages.
Laufs, U. et al., "Rosuvastatin, a new HMG-CoA reductase inhibitor, upregulates endothelial nitric oxide synthase and protects from ischemic stroke in mice," Brain Research, vol. 942, No. 1-2, Jun. 28, 2002, 8 pages.
Jones, S. et al., "Direct Vascular and Cardioprotective Effects of Rosuvastatin, a New HMG-CoA Reductase Inhibitor," Journal of the American College of Cardiology, vol. 40, No. 6, Sep. 18, 2002, 7 pages.
Di Napoli, P. et al., "Chronic treatment with rosuvastatin modulates nitric oxide synthase expression and reduces ischemia-reperfusion injury in rat hearts," Cardiovascular Research, vol. 66, No. 3, Jun. 1, 2005, Published Online Mar. 2, 2005, 10 pages.
Gupta, A. et al., "The HIV Protease Inhibitor Nelfinavir Downregulates Akt Phosphorylation by Inhibiting Proteasomal Activity and Inducing the Unfolded Protein Response," Neoplasia, vol. 9, No. 4, Apr. 2007, 8 pages.
Kosmidou, I. et al., "Statin Treatment and 3' Polyadenylation of eNOS mRNA," Arteriosclerosis, Thrombosis, and Vascular Biology, vol. 27, No. 12, Dec. 2007, Published Online Oct. 4, 2007, 12 pages.
Plastaras, J. et al., "Validation and toxicity of PI3K/Akt pathway inhibition by HIV protease inhibitors in humans," Cancer Biology & Therapy, vol. 7, No. 4, Apr. 2008, 8 pages.
Ghosh-Choudhury, N. et al., "Simvastatin Induces Derepression of PTEN Expression via NFkB to Inhibit Breast Cancer Cell Growth," Cell Signal, vol. 22, No. 5, May 2010, Published Online Jan. 11, 2010, 23 pages.
Fleming, G. et al., "Phase II trial of temsirolimus in patients with metastatic breast cancer," Breast Cancer Research and Treatment, vol. 136, No. 2, Nov. 2012, Published Online Jan. 13, 2012, 18 pages.

(Continued)

*Primary Examiner* — Kortney L. Klinkel
*Assistant Examiner* — Ibrahim D Bori
(74) *Attorney, Agent, or Firm* — McCoy Russell LLP

(57) ABSTRACT

The present disclosure relates to a method of treating cancer using a composition comprising Nelfinavir, Metformin, Rosuvastatin, optionally along with a pharmaceutically acceptable excipient. The said composition is used for the treatment of cancer caused due to aberration in PTEN gene, optionally along with aberration in TP53 gene and related genes selected from group comprising PI3K, CDKN2A, MDM2 and MDM4.

7 Claims, 9 Drawing Sheets

(56) References Cited

PUBLICATIONS

Kraus, M. et al., "Nelfinavir augments proteasome inhibition by bortezomib in myeloma cells and overcomes bortezomib and carfilzomib resistance," Blood Cancer Journal, vol. 4, No. e103, Mar. 1, 2013, 9 pages.
Iglesias, D. et al., "Another Surprise from Metformin: Novel Mechanism of Action via K-Ras Influences Endometrial Cancer Response to Therapy," Molecular Cancer Therapeutics, vol. 12, No. 12, Dec. 2013, Published Online Sep. 27, 2013, 10 pages.
Kushchayeva, Y. et al., "The HIV Protease Inhibitor Nelfinavir Down-Regulates RET Signaling and Induces Apoptosis in Medullary Thyroid Cancer Cells," Journal of Clinical Endocrinology and Metabolism, vol. 99, No. 5, May 2014, Published Online Jan. 31, 2014, 19 pages.
ISA European Patent Office, International Search Report Issued in Application No. PCT/IB2015/053269, dated Aug. 10, 2015, WIPO, 3 pages.

\* cited by examiner

COMBINATION OF NELFINAVIR, METFORMIN AND ROSUVASTATIN FOR TREATING CANCER CAUSED BY ABERRATIONS IN PTEN/TP53

CROSS REFERENCE TO RELATED APPLICATIONS

The present application is a U.S. National Phase of International Patent Application Serial No. PCT/IB2015/053269, entitled "COMBINATION OF NELFINAVIR, METFORMIN AND ROSUVASTATIN FOR TREATING CANCER CAUSED BY ABERRATIONS IN PTEN/TP53," filed on May 5, 2015. International Patent Application Serial No. PCT/IB2015/053269 claims priority to Indian Patent Application No. 2255/CHE/2014, filed on May 5, 2014. The entire contents of each of the above-cited applications are hereby incorporated by reference in their entirety for all purposes.

TECHNICAL FIELD

The present disclosure relates to the field of Cancer therapeutics. Particularly, the present disclosure provides a composition comprising Nelfinavir, Metformin and Rosuvastatin optionally along with a pharmaceutically acceptable excipient for the treatment of cancer caused due to aberration in PTEN gene, optionally along with aberration in TP53 gene and related genes selected from group comprising PI3K, CDKN2A, MDM2 and MDM4.

BACKGROUND OF THE DISCLOSURE

Phosphatase and Tensin Homolog or PTEN is a tumor suppressor gene. It is also known as mutated in multiple advanced cancer 1 (MMAC1). It is one of the most commonly mutated of all tumour suppressor genes, and if not mutated, it is often suppressed or downregulated. Somatic PTEN mutations and deletions, and inactivation of PTEN by methylation or microRNA silencing, are common in multiple tumour types. PTEN hamartoma tumour syndrome (PHTS) is a group of syndromes characterized by benign growths and a high risk for cancers of the breast, endometrium and thyroid. Cowden syndrome is the best characterized of these and 85% of patients have germline PTEN mutations. The range of abnormalities in patients with PHTS varies from patient to patient. Tumors associated with alteration of PTEN gene include the classical PHTS-associated tumours like breast, endometrium and thyroid, and also tumours of the central nervous system, prostate, lung, pancreas, liver and adrenal glands, as well as melanoma, leukaemia and lymphoma. An analysis of PTEN gene alteration in different cancer from COSMIC website is below:

| Primary tissue | % Mutated |
| --- | --- |
| Central nervous system | 50 |
| Endometrium | 40 |
| Prostate | 40 |
| Skin | 25 |
| Testis | 25 |
| Biliary tract | 20 |
| Urinary tract | 16.67 |
| Breast | 16.28 |
| Kidney | 14.29 |
| Ovary | 13.64 |
| Haematopoietic and lymphoid tissue | 11.9 |
| Soft tissue | 11.11 |

-continued

| Primary tissue | % Mutated |
| --- | --- |
| Lung | 9.21 |
| Thyroid | 9.09 |
| Bone | 8.82 |
| Cervix | 7.69 |
| Stomach | 4.76 |
| Upper aerodigestive tract | 4.55 |
| Autonomic ganglia | 3.03 |
| Large intestine | 2.63 |

PTEN is a phosphatase and its lipid phosphatase activity dephosphorylates the 3-phosphoinositide products of PI3K. 3-phosphoinositides can activate important survival kinases, such as phosphoinositide-dependent kinase 1 (PDK1; encoded by PDPK1) and AKT. Change in the phosphatase activity or deletion/downregulation of PTEN gene will result in hyper-activated AKT signalling. Other aberrations as in PI3K gene can also mimic the PTEN effect resulting in high AKT signaling. This hyper-activated AKT signalling will affect different processes such as cell cycle progression, metabolism, migration, apoptosis, transcription and translation. Highly activated AKT also confers resistance to different chemotherapy. PTEN mutation is also associated with the resistance to different targeted therapies, for example PTEN is associated with resistance to anti-HER2 therapy and anti-EGFR therapy in Breast cancer and Colorectal cancer respectively. PTEN mutated cells have also been shown to give resistance to MEK inhibitors in KRAS mutated cells.

Though preclinical studies have shown that mTOR inhibitors as single agents have shown preclinical success in PTEN mutated profiles, in clinical trial these inhibitors have shown limited efficacy and evidences are less of PTEN mutation and mTOR inhibitor sensitivity (Fleming et. al. "Phase II trial of temsirolimus in patients with metastatic breast cancer". Breast Cancer ResTreat. 2012 November; 136(2):355-63. doi: 10.1007/s10549-011-1910-7. Epub 2012 Jan. 13. PMID: 22245973).

In addition to aberrations in PTEN gene, TP53 is another tumor suppressor gene that is widely known to be deleted or mutated or inactivated in a large percentage of all cancers. Presence of TP53 gene aberration in a cancer is related to a bad prognosis and greater severity of the disease with minimal treatment options available.

Thus, as observed above, the existing standard of care does not work on a large section of patients harboring mutations in PTEN and P53 gene. Even chemotherapy has not been found to be effective on these tumors. Single agent therapies have been used as therapies or suggested for use as therapies for cancer treatment for the purpose of improving one or more undesirable symptoms associated with the disease states or for slowing the progression (worsening) of the symptoms. However, the success achieved with the single agents has been limited and hence improved treatment protocols for this complex and devastating disorder especially in the subset of tumors harboring these mutations, are greatly needed. A safe and effective treatment that could alleviate suffering and improve outcomes would be a significant medical advance for cancer treatment and potentially for the treatment of other end-stage diseases as well.

The present invention addresses the drawbacks of existing therapies by providing a composition and a method of treatment of such cancers using the composition.

STATEMENT OF THE DISCLOSURE

Accordingly, the present disclosure relates to a method for treating cancer caused by aberration in PTEN gene, optionally along with aberration in TP53 gene in a subject in need or want of relief thereof, the method comprising administering to the subject a composition comprising: i) Nelfinavir; ii) Metformin; and iii) Rosuvastatin; optionally along with a pharmaceutically-acceptable excipient; use of a composition comprising Nelfinavir, Metformin and Rosuvastatin optionally along with a pharmaceutically acceptable excipient, in the preparation of a medicament for the treatment of cancer caused by aberration in PTEN gene, optionally along with aberration in TP53 gene; a method of inhibiting cancer cells/inducing cytotoxicity in cancer cells/modulating markers in cancer cells, wherein cancer is caused by aberration in PTEN gene, optionally along with aberration in TP53 gene, said method comprising act of contacting the cancer cells with a composition comprising Nelfinavir, Metformin and Rosuvastatin, optionally along with a pharmaceutically acceptable excipient; and a composition comprising Nelfinavir, Metformin and Rosuvastatin optionally along with a pharmaceutically acceptable excipient.

BRIEF DESCRIPTION OF THE ACCOMPANYING FIGURES

DETAILED DESCRIPTION OF THE DISCLOSURE

Figure 1A:
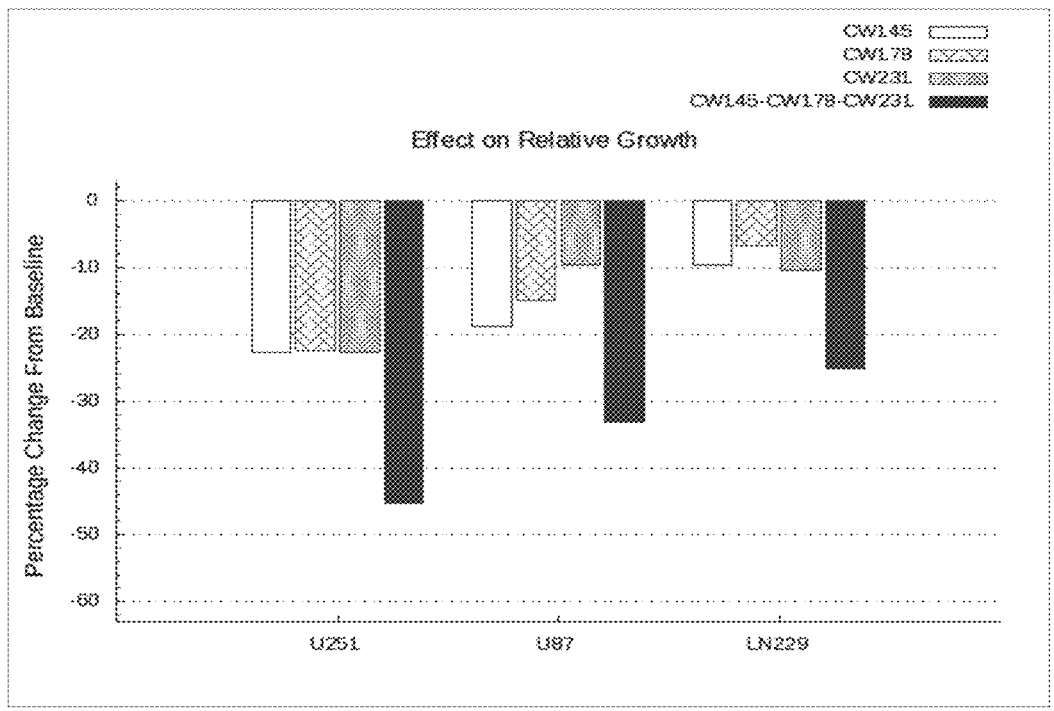
FIG. 1A depicts the impact of Single vs. Triple combination comprising of drugs CW145 (Nelfinavir), CW178 (Metformin) and CW231 (Rosuvastatin) at IC20 concentration on Relative Growth phenotype in U251 cell line (having mutation in PTEN, TP53 and CDKN2A), U87 cell line (having PTEN, CDKN2A mutation) and LN229 (having TP53, CDKN2A mutation).

The present disclosure relates to a method of treating cancer using a composition.

In an embodiment, the present disclosure relates to a method of treating cancer using a composition comprising Nelfinavir, Metformin and Rosuvastatin, optionally along with pharmaceutically acceptable excipients.

In another embodiment of the present disclosure, the cancer/cancer cells have aberration in PTEN gene optionally along with aberration in TP53 gene and related genes selected from a group comprising PI3K, CDKN2A, MDM2 and MDM4.

In another embodiment of the present disclosure, aberration includes but not limiting to mutation, deletion and amplification.

The present disclosure relates to a method for treating cancer caused by aberration in PTEN gene, optionally along with aberration in TP53 gene in a subject in need or want of relief thereof, the method comprising administering to the subject a composition comprising:
  i) Nelfinavir;
  ii) Metformin; and
  iii) Rosuvastatin;
  optionally along with a pharmaceutically-acceptable excipient.

In an embodiment of the present disclosure, the aberration in PTEN is optionally associated with aberration in PI3K gene.

In an embodiment of the present disclosure, the aberration in TP53 is associated with aberration in genes selected from a group comprising CDKN2A, MDM2, MDM4 and combinations thereof.

In an embodiment of the present disclosure, the pharmaceutically acceptable excipient is selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material, spheronization agents and any combination thereof.

In an embodiment, the present disclosure relates to a method for treating cancer caused by aberration in PTEN gene and TP53 gene in a subject in need or want of relief thereof, the method comprising administering to the subject a composition comprising Nelfinavir, Metformin and Rosuvastatin optionally along with a pharmaceutically-acceptable excipient. The present disclosure relates to use of a composition comprising Nelfinavir, Metformin and Rosuvastatin optionally along with a pharmaceutically acceptable excipient, in the preparation of a medicament for the treatment of cancer caused by aberration in PTEN gene, optionally along with aberration in TP53 gene.

In an embodiment of the present disclosure, the aberration in PTEN is optionally associated with aberration in PI3K gene.

In an embodiment of the present disclosure, the aberration in TP53 is associated with aberration in genes selected from a group comprising CDKN2A, MDM2, MDM4 and combinations thereof.

In an embodiment of the present disclosure, the pharmaceutically acceptable excipient is selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material, spheronization agents and any combination thereof.

The present disclosure relates to a method of inhibiting cancer cells/inducing cytotoxicity in cancer cells/modulating markers in cancer cells, wherein cancer is caused by aberration in PTEN gene, optionally along with aberration in TP53 gene, said method comprising act of contacting the cancer cells with a composition comprising Nelfinavir, Metformin and Rosuvastatin, optionally along with a pharmaceutically acceptable excipient.

The present disclosure relates to a method of reducing relative growth of cancer cells, wherein cancer is caused by aberration in PTEN gene, optionally along with aberration in TP53 gene, said method comprising act of contacting the cancer cells with a composition comprising Nelfinavir, Metformin and Rosuvastatin, optionally along with a pharmaceutically acceptable excipient.

In an embodiment of the present disclosure, the aberration in PTEN is optionally associated with aberration in PI3K gene.

In an embodiment of the present disclosure, the aberration in TP53 is associated with aberration in genes selected from a group comprising CDKN2A, MDM2, MDM4 and combinations thereof.

The present disclosure relates to a composition comprising Nelfinavir, Metformin and Rosuvastatin optionally along with pharmaceutically acceptable excipient.

In an embodiment of the present disclosure, the pharmaceutically acceptable excipient is selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material, spheronization agents and any combination thereof.

In an embodiment of the present disclosure, the composition is in a dosage form selected from a group comprising feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, cream, drop, dispersible powder or granule, emulsion in hard or soft gel capsule, syrup, phytoceutical, nutraceutical and combination thereof.

In an embodiment of the present disclosure, the composition is a dosage form having an immediate release, a controlled release or a sustained delayed release mechanism.

In an embodiment of the present disclosure, the composition is a dosage form formulated for mode of administration selected from a group comprising intravenous, subcutaneous, intramuscular, oral, rectal, aerosol, parenteral, ophthalmic, pulmonary, transdermal, vaginal, otic, nasal, topical administration and combination thereof.

The present disclosure also relates to a kit comprising Nelfinavir, Metformin and Rosuvastatin optionally along pharmaceutically acceptable excipient.

In yet another embodiment of the present disclosure, Nelfinavir used in the composition is an AKT inhibitor as well as HIV protease inhibitor.

In still another embodiment of the present disclosure, Metformin used in the composition is an AMPK agonist.

In still another embodiment of the present disclosure, Rosuvastatin used in the composition is a prenylation inhibitor.

In still another embodiment of the present disclosure, the composition comprises Nelfinavir at a concentration ranging from about 625 mg to about 2500 mg, Metformin at a concentration ranging from about 1000 mg to about 1500 mg and Rosuvastatin at a concentration ranging from about 5 mg to about 40 mg.

In an embodiment, the present disclosure relates to three drug combination, which provides multi-targeted combination therapeutic approach to suppress and cure symptoms associated with Cancers. The drug combinations are validated predicatively using Virtual Tumor Cell Platform as described herein followed by validation experimentally in human tumor cell lines.

In an embodiment, the present disclosure provides three-drug combination, which provides multi-targeted combination therapeutic approach to suppress and cure symptoms associated with PTEN mutant Cancers optionally along with aberration in P53 gene and related genes selected from group comprising PI3K, CDKN2A, MDM2 and MDM4. The drug combinations are validated predicatively using Virtual Tumor Cell Platform as described herein followed by validation experimentally in human tumor cell lines.

In an embodiment, the present disclosure focuses on tumors where PI3K/AKT/mTOR signaling axis is highly activated such as tumors associated with PTEN mutant Cancers optionally along with aberration in TP53 gene and related genes selected from group comprising PI3K, CDKN2A, MDM2 and MDM4.

AKT is highly activated in certain cancers that carry mutations in proteins converging on the PI3K/AKT axis. Examples of such tumors include for example those having loss of function mutation/copy number loss in PTEN gene, gain of function mutation or copy number gain in PI3K isoforms, IRS isoforms etc.

To illustrate the downstream impact of high PI3K/AKT signaling axis, the scenario with PTEN mutation is explained further. PTEN is a tumor suppressor gene which carries out the dephosphorylation of PIP3 to PIP2, leading to inactivation of AKT/mTOR signaling pathway. PTEN mutation or PTEN loss results in accumulation of PIP3 which in turn activates AKT and PDK1. PDK1 carries out further phosphorylation and activation of AKT. The constitutively activated AKT drives cell survival, proliferation and cellular metabolism through its downstream signaling such as inhibitory phosphorylation of downstream pro-apoptotic proteins like FOXO, GSK3B etc, activation of mTORC1 which phosphorylates p70 ribosomal protein S6 kinase (S6K) and eukaryotic translation-initiation factor 4E (eIF4E)-binding protein 1 (4EBP1) to activate protein translation and cell proliferation. mTORC1 further activates HIF1 which is a key transcription factor for many cellular metabolism genes and also plays an important role in angiogenesis.

In an embodiment of the present disclosure, nelfinavir is represented as CW145.

In another embodiment of the present disclosure, metformin is represented as CW178.

In yet another embodiment of the present disclosure, rosuvastatin is represented as CW231.

CW145 class of drug (Nelfinavir) is a specific inhibitor of HIV protease that also inhibits AKT. CW145 are orally available drugs developed to specifically inhibit the HIV aspartyl protease, a retroviral enzyme that cleaves the viral gag-pol polyprotein necessary for the production of infectious viral particles and that lacks mammalian close homologs. These drugs are approved for anti-viral therapy for HIV infected patients. However, it is determined that these drugs can cause insulin resistance due to inhibition of AKT signaling. Clinical studies demonstrated that HIV positive patients receiving these drugs had an inhibition of their phosphorylated AKT levels. Thus, these drugs are tested in tumor cells and found to demonstrate anti-neoplastic effect, primarily through their inhibition of AKT.

CW178 class of drug (Metformin) is an activator of AMPK. AMPK is an energy sensor enzyme which is activated in cells under metabolic stress. Activated AMPK helps the cells to survive under nutrient deprived conditions by inhibiting cell proliferation. AMPK is known to phosphorylate and activate TSC1-TSC2 complex which is an endogenous inhibitor of mTOR. AMPK also causes an inhibitory phosphorylation of IRS1 at ser-789 position. So in a cancer profile having highly-activated PI3K/AKT/mTOR signaling axis, such as those with PTEN mutation/loss or activated IRS, the activation of AMPK will result in inhibition of the constitutively active mTORC1 thereby, reducing cell proliferation.

The CW231 class of drug (Rosuvastatin) is a prenylation inhibitor, specifically 3-hydroxy-3-methylglutaryl coenzyme A (HMG-CoA) reductase inhibitor. By inhibiting HMG-CoA reductase, CW231 inhibits process of prenylation, a post-translational modification of many GTPases. The process of prenylation facilitates protein-protein/protein-membrane interactions of important proteins like RAS, RHO, RAC1, CDC42 and RHEB. In case of cancers having high activation of PI3K/AKT/mTOR axis, inhibition of RHEB prenylation would cause reduction in tumor growth.

In an embodiment of the present disclosure, the three drug combination of CW145 (Nelfinavir), CW178 (Metformin) and CW231 (Rosuvastatin) is the most effective when the tumor cells have aberration of PTEN along with aberration of TP53. This is because, in the presence of wild-type p53, combination may induce autophagy to some extent which can provide cytoprotective effect via recycling of amino acids etc. Autophagy induction has been reported to support survival of cells under stress conditions. The autophagy induction happen in the presence of WT p53 when treated with the combination of above drugs because p53 transcribes ULK1 which is known to induce autophagy via activation of BECLIN. AMPK phosphorylates and activates ULK1. mTOR is known to inhibit ULK1. So, in combination, activation of AMPK by CW178 and inhibition of AKT/mTOR by CW145 induce ULK1 which will activate BECLIN1 complex and activate autophagy. On the contrary, presence of mutated p53 or deletion of p53 will support the response to the combination because mutated/deleted p53 will not be able to induce ULK1 transcription and hence cytoprotective autophagy will not get triggered. Loss of other proteins needed for induction of autophagy may due to similar reason increase the effectiveness of the combination.

As used herein, the term, "CW145178231," refers to a combination of CW145 compound-Nelfinavir, CW178 compound-Metformin and CW231 compound-Rosuvastatin in any amount, ratio, concentration, or order thereof.

In an embodiment of the present disclosure, the composition for treatment of cancer comprises compounds included in Table 1 below:

Table 1: Indicates the Synonyms, IUPAC Names and Structures of Nelfinavir, Metformin and Rosuvastatin

| Compound | Synonyms | IUPAC Name | Structure |
|---|---|---|---|
| Nelfinavir | Viracept (TN), VRX496, NelfinavirMonomethane-Sulfonate | (3S,4aS,8aS)-N-tert-butyl-2-[(2R,3R)-2-hydroxy-3-[(3-hydroxy-2-methylbenzoyl)amino]-4-phenylsulfanylbutyl]-3,4,4a,5,6,7,8,8a-octahydro-1H-isoquinoline-3-carboxamide | 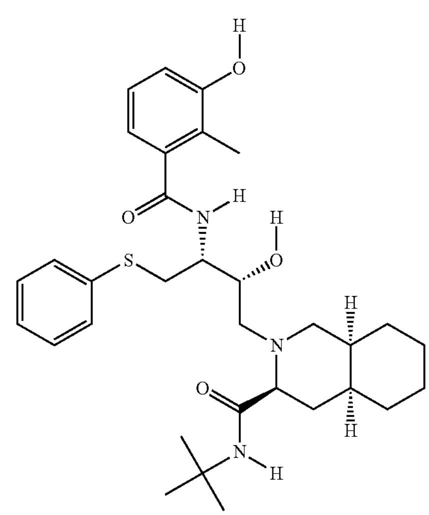 [SMILES: Cc1c(O)cccc1C(=O)N[C@@H](CSc1ccccc1)[C@H](O)CN1C[C@H]2CCCC[C@H]2C[C@H]1C(=O)NC(C)(C)C] |

-continued

| Compound | Synonyms | IUPAC Name | Structure |
|---|---|---|---|
| Metformin | Metformin HCL, metformin hydrochloride | 1-carbamimidamido-N,N-dimethyl-methanimidamide | 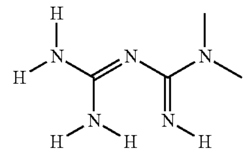 |
| Rosuvastatin | Creston | (E,3R,5S)-7-[4-(4-fluorophenyl)-2-[methyl(methylsulfonyl)amino]-6-propan-2-ylpyrimidin-5-yl]-3,5-dihydroxyhept-6-enoic acid | 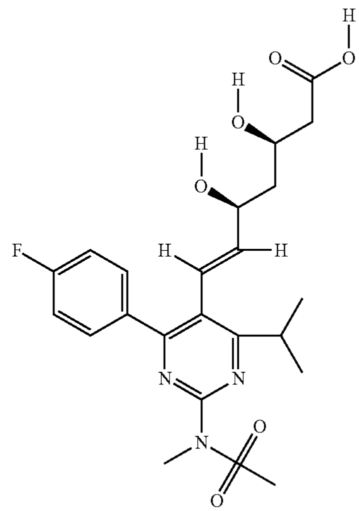 |

In an embodiment, the disclosure provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In an embodiment, a pharmaceutically-acceptable salt is a metal salt. In an embodiment, a pharmaceutically-acceptable salt is an ammonium salt.

Metal salts can arise from the addition of an inorganic base to a compound of the disclosure. The inorganic base consists of a metal cation paired with a basic counterion, such as, for example, hydroxide, carbonate, bicarbonate or phosphate. The metal can be an alkali metal, alkaline earth metal, transition metal, or main group metal. In an embodiment, the metal is lithium, sodium, potassium, cesium, cerium, magnesium, manganese, iron, calcium, strontium, cobalt, titanium, aluminum, copper, cadmium or zinc.

In an embodiment of the present disclosure, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt or a zinc salt. Ammonium salts can arise from the addition of ammonia or an organic amine to a compound of the disclosure. In an embodiment, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In an embodiment of the present disclosure, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the disclosure. In an embodiment, the acid is organic. In another embodiment, the acid is inorganic. In an embodiment, the acid is hydrochloric acid, hydrobromic acid, hydroiodic acid, nitric acid, nitrous acid, sulfuric acid, sulfurous acid, phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In an embodiment of the present disclosure, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

In an embodiment of the present disclosure, excipients are selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material, spheronization agents and any combination thereof.

Pharmaceutical Compositions

The present disclosure further relates to a process for obtaining a composition comprising of i) CW145-Nelfinavir, ii) CW178-Metformin and iii) CW231-Rosuvastatin, optionally along with pharmaceutically acceptable excipient(s), said process comprising act of combining said compounds in any order thereof.

In an embodiment of the present disclosure, the pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by any form and route known in the art including, for example, intravenous, subcutaneous, intramuscular, oral, rectal, aerosol, parenteral, ophthalmic, pulmonary, transdermal, vaginal, otic, nasal, and topical administration.

In an embodiment of the present disclosure, the pharmaceutical composition can be administered in a local or systemic manner, for example, through injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

In an embodiment of the present disclosure, pharmaceutical compositions for oral administration can be formulated readily by combining the active compounds with pharmaceutically acceptable carriers or excipients well known in the art. Such carriers can be used to formulate tablets, powders, pills, dragees, capsules, liquids, gels, syrups, elixirs, slurries, suspensions and the like, for oral ingestion by a subject.

In an embodiment of the present disclosure, pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which may optionally contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

In an embodiment of the present disclosure, pharmaceutical preparations which can be used orally include push-fit capsules made of gelatin, as well as soft, sealed capsules made of gelatin and a plasticizer, such as glycerol or sorbitol. In an embodiment, the capsule comprises a hard gelatin capsule comprising one or more of pharmaceutical, bovine, and plant gelatins. A gelatin can be alkaline processed. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. Stabilizers can be added. All formulations for oral administration are provided in dosages suitable for such administration.

In an embodiment of the present disclosure, the compositions can be tablets, lozenges, or gels for buccal or sublingual administration.

In an embodiment of the present disclosure, parental injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

In an embodiment of the present disclosure, the active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In an embodiment of the present disclosure, formulations suitable for transdermal administration of the active compounds can employ transdermal delivery devices and transdermal delivery patches, and can be lipophilic emulsions or buffered aqueous solutions, dissolved and/or dispersed in a polymer or an adhesive. Such patches may be constructed for continuous, pulsatile, or on demand delivery of pharmaceutical compounds. Transdermal delivery can be accomplished by means of iontophoretic patches and the like. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and means to secure the device to the skin.

In an embodiment of the present disclosure, the active compounds for administration by inhalation can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

In an embodiment of the present disclosure, the compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as a mixture of fatty acid glycerides, optionally in combination with cocoa butter, is first melted.

In practicing the methods of treatment or use provided herein, therapeutically-effective amounts of the compounds described herein are administered in pharmaceutical compositions to a subject having a disease or condition to be treated.

In an embodiment, the subject is a mammal such as a human. A therapeutically-effective amount can vary widely depending on the severity of the disease, the age and relative health of the subject, the potency of the compounds used and other factors. The compounds can be used singly or in combination with one or more therapeutic agents as components of mixtures.

In an embodiment of the present disclosure, pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising compounds described herein can be manufactured in a conventional manner, for example, by means of conventional mixing, dissolving, granulating, dragee-making, levigating, emulsifying, encapsulating, entrapping or compression processes.

In an embodiment of the present disclosure, the pharmaceutical compositions can include at least one pharmaceutically acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

In an embodiment of the present disclosure, methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of non-toxic, auxiliary substances, such as wetting or emulsifying agents, pH buffering agents, and other pharmaceutically-acceptable additives.

In an embodiment of the present disclosure, compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellarvesicle (SUV), and the large unilamellar vesicle (LUV). Liposomal physicochemical properties can be modulated to optimize penetration through biological barriers and retention at the site of administration, and to prevent premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

In an embodiment of the present disclosure, compounds can be delivered via antibody-drug conjugates (ADCs) technology. Here, drugs are conjugated/fused to tumor-specific antibodies so as to deliver the drug to the site of tumor and increase their therapeutic efficacy. ADCs have been developed for targeted delivery of anti-cancer drugs to tumor in the patient body with the aim of bypassing the morbidity common to conventional drug delivery.

In an embodiment of the present disclosure, non-limiting examples of dosage forms suitable for use in the disclosure include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals and any combination thereof.

In an embodiment of the present disclosure, non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material and spheronization agents, and any combination thereof.

In an embodiment of the present disclosure, a composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, granular masses, and the like.

In an embodiment of the present disclosure, compositions of the disclosure can be delivered through a time-controlled delivery system. An example of a suitable time-controlled delivery system is the PULSINCAP® system, or a variant thereof. The time-controlled delivery system can further comprise pH-dependent systems, microbially-triggered delivery systems, or a combination thereof. The time-controlled system may comprise a water insoluble capsule body enclosing a drug reservoir. The capsule body can be closed at one end with a hydrogel plug. The hydrogel plug can comprise swellable polymers, erodible compressed polymers, congealed melted polymers, enzymatically-controlled erodible polymers, or a combination thereof. The swellable polymers can include polymethacrylates. Non-limiting examples of erodible compressed polymers include hydroxypropyl methylcellulose, polyvinyl alcohol, polyvinyl acetate, polyethylene oxide, and combinations thereof. Non-limiting examples of congealed melted polymers include saturated polyglycolated glycerides, glycerylmonooleate, and combinations thereof. Non-limiting examples of enzymatically-controlled erodible polymers include polysaccharides; amylose; guar gum; pectin; chitosan; inulin; cyclodextrin; chondroitin sulphate; dextrans; locust bean gum; arabinogalactan; chondroitin sulfate; xylan; calcium pectinate; pectin/chitosan mixtures; amidated pectin; and combinations thereof.

In an embodiment of the present disclosure, the time-controlled delivery system can comprise a capsule, which further comprises an organic acid. The organic acid can be filled into the body of a hard gelatine capsule. The capsule can be coated with multiple layers of polymers. The capsule can be coated first with an acid soluble polymer, such as EUDRAGIT® E, then with a hydrophilic polymer, such as hydroxypropyl methylcellulose, and finally with an enteric coating, such as EUDRAGIT® L.

In an embodiment of the present disclosure, an additional example of a suitable time-controlled delivery system is the CHRONOTROPIC® system, or a variant thereof, which comprises a drug core that is coated with hydroxypropyl methylcellulose and an outer enteric film.

In an embodiment of the present disclosure, an additional example of a suitable time-controlled delivery system is the CODES' system, or a variant thereof. The time-controlled delivery system can comprise a capsule body, which can house, for example, a drug-containing tablet, an erodible tablet, a swelling expulsion excipient, or any combination thereof. The capsule can comprise an ethyl cellulose coat. The time-controlled delivery system can comprise two different sized capsules, one inside the other. The space between the capsules can comprise a hydrophilic polymer. The drug-containing core canay be housed within the inner capsule. The drug delivery system can comprise an impermeable shell, a drug-containing core, and erodible outer layers at each open end. When the outer layers erode, the drug is released.

In an embodiment of the present disclosure, examples of suitable multiparticulate drug delivery systems include DIFFUCAPS®, DIFFUTAB®, ORBEXA®, EURAND MINIT-ABS®, MICROCAPS® and variants thereof. The drug delivery system can comprise multiparticulate beads, which are comprised of multiple layers of the drug compound, excipients, and release-controlling polymers. The multiparticulate beads can comprise an organic acid or alkaline buffer. The multiparticulate beads can comprise a solid solution of the drug compound and crystallization inhibitor. The drug delivery system can comprise a matrix tablet containing water-soluble particles and the drug compound. The matrix tablet can further comprise hydrophilic and hydrophobic polymers. In some multiparticulate delivery systems, particles in the micron size range are used. In some multiparticulate delivery systems, nanoparticle colloidal carriers composed of natural or synthetic polymers are used.

In an embodiment of the present disclosure, a controlled release formulation is a delayed release form. A delayed release form can be formulated to delay a compound's action for an extended period of time. A delayed release form can be formulated to delay the release of an effective dose of one or more compounds, for example, for about 4, about 5, about 6, about 7, about 8, about 9, about 10, about 11, about 12, about 13, about 14, about 15, about 16, about 17, about 18, about 19, about 20, about 21, about 22, about 23, or about 24 hours.

In an embodiment of the present disclosure, a controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 5, about 6, about 7, about 8, about 9, about 10, about 11, about 12, about 13, about 14, about 15, about 16, about 17, about 18, about 19, about 20, about 21, about 22, about 23, or about 24 hours.

In an embodiment of the present disclosure, a tablet providing a sustained or controlled release can comprise a first layer containing one or two of the compounds described herein, and a tablet core containing one or two other compounds. The core can have a delayed or sustained dissolution rate. Other exemplary embodiments can include a barrier between the first layer and core, to limit drug release from the surface of the core. Barriers can prevent dissolution of the core when the pharmaceutical formulation is first exposed to gastric fluid. For example, a barrier can comprise a disintegrant, a dissolution-retarding coating (e.g., a polymeric material, for example, an enteric polymer such as a Eudragit polymer), or a hydrophobic coating or film, and can be selectively soluble in either the stomach or intestinal fluids. Such barriers permit the compounds to leach out slowly. The barriers can cover substantially the whole surface of the core.

Dosing

In an embodiment of the present disclosure, pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged tablets or capsules, and powders in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

In an embodiment of the present disclosure, the compound described herein can be present in a composition in a range of from about 1 mg to about 2500 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

In an embodiment of the present disclosure, the compound described herein can be present in a composition in an amount of about 1 mg, about 5 mg, about 10 mg, about 20 mg, about 25 mg, about 50 mg, about 75 mg, about 100 mg, about 150 mg, about 200 mg, about 250 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, 2300 mg, 2400 mg or 2500 mg In an embodiment of the present disclosure, the composition comprises from about 625 mg/day to about 2500 mg/day of Nelfinavir, from about 20 mg/day to about 80 mg/day of Rosuvastatin and from about 500 mg/day to about 1500 mg/day of Metformin.

In an embodiment of the present disclosure, the compound described herein is present in a composition in an amount that is a fraction or percentage of the maximum tolerated amount. The maximum tolerated amount can be as determined in a subject, such as a mouse or human. The fraction can be expressed as a ratio of the amount present in the composition divided by the maximum tolerated dose. The ratio can be from about 1/20 to about 1/1. The ratio can be about 1/20, about 1/19, about 1/18, about 1/17, about 1/16, about 1/15, about 1/14, about 1/13, about 1/12, about 1/11, about 1/10, about 1/9, about 1/8, about 1/7, about 1/6, about 1/5, about 1/4, about 1/3, about 1/2, or about 1/1. The ratio can be 1/20, 1/19, 1/18, 1/17, 1/16, 1/15, 1/14, 1/13, 1/12, 1/11, 1/10, 1/9, 1/8, 1/7, 1/6, 1/5, 1/4, 1/3, 1/2, or 1/1. The ratio can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The ratio can be in a range from about 5% to about 100%, from about 10% to about 100%, from about 5% to about 80%, from about 10% to about 80%, from about 5% to about 60%, from about 10% to about 60%, from about 5% to about 50%, from about 10% to about 50%, from about 5% to about 40%, from about 10% to about 40%, from about 5% to about 20%, or from about 10% to about 20%.

The foregoing ranges are merely suggestive. Dosages can be altered depending on a number of variables, including, for example, the activity of the compound used, the disease or condition to be treated, the mode of administration, the requirements of the individual subject, severity of the disease or condition being treated, and the judgment of the practitioner.

In an embodiment of the present disclosure, dose can be modulated to achieve a desired pharmacokinetic or pharmacodynamics profile, such as a desired or effective blood profile, as described herein.

Pharmacokinetic and Pharmacodynamic Measurements

In an embodiment of the present disclosure, pharmacokinetic and pharmacodynamic data can be obtained by techniques known in the art. Appropriate pharmacokinetic and pharmacodynamic profile components describing a particular composition can vary due to the inherent variation in pharmacokinetic and pharmacodynamic parameters of drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

In an embodiment of the present disclosure, the pharmacokinetic parameters can be any parameters suitable for describing a compound disclosed herein. For example, the $C_{max}$ can be not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other $C_{max}$ appropriate for describing a pharmacokinetic profile of a compound described herein.

In an embodiment of the present disclosure, the $T_{max}$ of a compound described herein can be, for example, not greater than about 0.5 hours, not greater than about 1.0 hours, not greater than about 1.5 hours, not greater than about 2.0 hours, not greater than about 2.5 hours, not greater than about 3.0 hours, or any other $T_{max}$ appropriate for describing a pharmacokinetic profile of a compound described herein.

In an embodiment of the present disclosure, the $AUC_{(0-inf)}$ of a compound described herein can be, for example, not less than about 250 ng·hr/mL, not less than about 500 ng·hr/mL, not less than about 1000 ng·hr/mL, not less than about 1500 ng·hr/mL, not less than about 2000 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, or any other $AUC_{(0-inf)}$ appropriate for describing a pharmacokinetic profile of a compound described herein.

In an embodiment of the present disclosure, the plasma concentration of a compound described herein about one hour after administration can be, for example, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a compound described herein.

In an embodiment of the present disclosure, the pharmacodynamic parameters can be any parameters suitable for describing compositions of the disclosure. For example, the pharmacodynamic profile can exhibit decreases in viability phenotype for the tumor cells or tumor size reduction in tumor cell lines or xenograft studies, for example, about 24 hours, about 48 hours, about 72 hours, or 1 week.

The present disclosure further relates to a method for treating a subject either suspected of having or having condition or a combination thereof, wherein said condition is selected from a group comprising solid tumor such as Pancreatic Cancer, Colorectal Cancer, Lung Cancer, tumors of central nervous system, Head and Neck Cancer, Breast cancer and Liquid tumor such as multiple myeloma, acute non lymphocytic leukemia and myelodysplasia, or any combination of conditions thereof, or wherein said aberration is in PTEN gene, optionally along with aberration in TP53 gene and related genes selected from group comprising PI3K, CDKN2A, MDM2 and MDM4, said method comprising act of administering to the subject a composition comprising nelfinavir, rosuvastatin and metformin, optionally along with pharmaceutically acceptable excipient.

In an embodiment of the present disclosure, the composition comprising Nelfinavir, Metformin and Rosuvastatin is administered at time interval ranging from about 1 second to about 64800 seconds;

In another embodiment of the present disclosure, each of the compounds in the composition is in ratio ranging from about IC10 dose to IC80.

In an embodiment of the present disclosure, oncology disease system of the present disclosure is a very comprehensive representation of the bio-molecular activity involved in the solid and liquid tumors. The system includes all the pathways and bio-molecular interactions in the key phenotypes of Cancer, such as viability, apoptosis, proliferation, angiogenesis and metastasis.

In an embodiment of the present disclosure, the Virtual Tumor Cell Platform of the present disclosure consists of a dynamic and kinetic representation of the signaling pathways underlying tumor physiology at the bio-molecular level with coverage on all the key tumor phenotypes including proliferation, viability, angiogenesis, metastasis, apoptosis, tumor metabolism and tumor microenvironment related to associated inflammation. The technology is a comprehensive coverage of protein players; associated gene and mRNA species with regard to tumor related signaling. The platform subset coverage includes signaling pathways comprising growth factors like EGFR, PDGFRA, FGFR, c-MET, VEGFR and IGF-1R, cell cycle regulators, mTOR signaling, p53 signaling cascade, cytokine pathways like IL1, IL4, IL6, IL12, IL15 TNF; TGF-b, hypoxia mediated regulation, angiogenic promoters, lipid mediators and tumor metabolism and others. It has a wide coverage of kinases and transcription factors associated with tumor physiology network. The modeling of the time-dependent changes in the fluxes of the constituent pathways is done utilizing modified ordinary differential equations (ODE) and mass action kinetics. The current version of the technology includes over 10000 biological species with over forty five thousand cross-talk interactions. The platform is prospectively and retrospectively validated against an extensive set of pre-defined in vitro and in vivo studies.

In an embodiment of the present disclosure, the starting control state of the system is based on normal epithelial cell physiology that is non-tumorigenic. The user can control the transition of the normal system to a neoplastic disease state aligning with specific tumor mutation profiles. This is accomplished as an example through over-expression of the tumorigenic genes like EGFR, IGF-1R; knock-downs of the tumor-suppressors like p53, PTEN; and increased states of hypoxia and oxidative stress. Knockdowns or over-expressions of biological species can be done at the expression or activity levels.

In an embodiment of the present disclosure, drugs are represented in this technology through explicit mechanism of action specification and the drug concentration in the virtual experiments is explicitly assumed to be post ADME (Absorption, Distribution, Metabolism, and Excretion). In an embodiment of the present disclosure, multiple virtual patient profiles can be generated by overlaying the functional impact of mutations. Therapeutics that is being designed is tested against this panel of virtual patients to understand the differential sensitivity of the therapy to the multiple patient profiles. This system of testing is the first step on the road to designing and tailoring therapies for individual patients.

In an embodiment of the present disclosure, composition and the process of preparing the composition for the purpose of improving one or more undesirable symptoms associated with the disease states or for slowing the progression (worsening) of one or more symptoms associated with the disease is provided.

Physicochemical Properties and Mechanism of Action CW145: (Table 1)
Name: Nelfinavir
Drug Bank Accession No: DB00220 (APRD00003)
Type: Small Molecule inhibitor
Groups: Approved
Description: Nelfinavir is an anti-viral compound that specifically inhibits the HIV aspartyl protease, a retroviral enzyme that cleaves the viral gag-pol polyprotein required for the production of infectious viral particles. This also has anti-neoplastic activity mediated through inhibition of AKT phosphorylation. At higher concentrations, Nelfinavir can inhibit the beta 2 (trypsin-like activity) subunit along with the beta 1 and beta 5 (chymotrypsin like activity) of the proteasome and induce endoplasmic reticulum stress. It is used in combination with other antiviral drugs in the treatment of HIV in both adults and children.

Brand names: Viracept
Indication: Used in combination with other antiviral drugs in the treatment of HIV in both adults and children.
Pharmacodynamics:—
HIV protease inhibitors such as Nelfinavir have been reported to cause AKT inhibition at 20 uM which is in the range of concentration of the drug achievable in plasma at therapeutically approved dosage. [PMID 23454896]. Inhibition of AKT phosphorylation at Ser473 has been reported to be an independent mechanism of drug action in this study as opposed to other papers that report AKT inhibition as a consequence of proteasome inhibition and consequent unfolded protein response. [PMID: 17460771]. However, direct/indirect inhibition of AKT by HIV protease inhibitors is well reported and has been seen in patients taking the medication. [PMID: 18285707]

Mechanism of action: HIV protease inhibitor, AKT inhibitor, Proteasome inhibitor
Absorption: Well absorbed following oral administration.
Metabolism: Primarily hepatic via cytochrome P450 (CYP450) enzymes. CYP3A and CYP2C19 appear to be the predominant enzymes that metabolize nelfinavir in humans. One major and several minor metabolites are found in plasma; the major oxidative metabolite has in vitro antiviral activity comparable to that of the parent drug.

Half-life: 3.5-5 hours

Route of elimination: The terminal half-life in plasma was typically 3.5 to 5 hours. The majority (87%) of an oral 750 mg dose containing 14C-nelfinavir was recovered in the feces; fecal radioactivity consisted of numerous oxidative metabolites (78%) and unchanged nelfinavir (22%). Only 1-2% of the dose was recovered in urine, of which unchanged nelfinavir was the major component.

Manufacturers: Hoffmann-La Roche

FDA Approval: Nelfinavir is an FDA approved drug.

CW178: (Table 1)

Name: Metformin

Drug Bank ID: DB00331 (APRD01099)

Type: Small Molecule Inhibitor

Group: approved

Dosage: Form—Tablet, Route—Oral, Strength—500 mg-2500 mg

Description: Metformin is a biguanideantihyperglycemic agent used for treating non-insulin-dependent diabetes mellitus (NIDDM). It improves glycemic control by decreasing hepatic glucose production, decreasing glucose absorption and increasing insulin-mediated glucose uptake. Metformin is the only oral antihyperglycemic agent that is not associated with weight gain. Metformin may induce weight loss and is the drug of choice for obese NIDDM patients. When used alone, metformin does not cause hypoglycemia; however, it may potentiate the hypoglycemic effects of sulfonylureas and insulin. Its main side effects are dyspepsia, nausea and diarrhea. Dose titration and/or use of smaller divided doses may decrease side effects. Metformin should be avoided in those with severely compromised renal function (creatinine clearance <30 ml/min), acute/decompensated heart failure, severe liver disease and for 48 hours after the use of iodinated contrast dyes due to the risk of lactic acidosis. Lower doses should be used in the elderly and those with decreased renal function. Metformin decreases fasting plasma glucose, postprandial blood glucose and glycosolated hemoglobin (HbA1c) levels, which are reflective of the last 8-10 weeks of glucose control. Metformin may also have a positive effect on lipid levels. In 2012, a combination tablet of linagliptin plus metformin hydrochloride was marketed under the name Jentadueto for use in patients when treatment with both linagliptin and metformin is appropriate.

Brand Name: Apo-Metformin, Fortamet, Gen-Metformin, Glucophage, Glucophage XR, GlumetzaGlycon, Mylan-Metformin, Novo-Metformin, Nu-Metformin, PMS-Metformin, Ran-Metformin, Ratio-Metformin, Riomet, Sandoz Metformin, Teva-Metformin Indication: For use as an adjunct to diet and exercise in adult patients (18 years and older) with NIDDM. It may also be used for the management of metabolic and reproductive abnormalities associated with polycystic ovary syndrome (PCOS). Jentadueto is for the treatment of patients when both linagliptin and metformin is appropriate.

Pharmacodynamics: Metformin is an oral antihyperglycemic agent that improves glucose tolerance in patients with NIDDM, lowering both basal and postprandial plasma glucose. Metformin is not chemically or pharmacologically related to any other class of oral antihyperglycemic agents. Unlike sulfonylureas, metformin does not produce hypoglycemia in either patients with NIDDM or healthy subjects and does not cause hyperinsulinemia. Metformin does not affect insulin secretion.

Mechanism of Action: Metformin's mechanisms of action differ from other classes of oral antihyperglycemic agents. Metformin decreases blood glucose levels by decreasing hepatic glucose production, decreasing intestinal absorption of glucose, and improving insulin sensitivity by increasing peripheral glucose uptake and utilization. These effects are mediated by the initial activation by metformin of AMP-activated protein kinase (AMPK), a liver enzyme that plays an important role in insulin signaling, whole body energy balance, and the metabolism of glucose and fats. Activation of AMPK is required for metformin's inhibitory effect on the production of glucose by liver cells. Increased peripheral utilization of glucose may be due to improved insulin binding to insulin receptors. Metformin administration also increases AMPK activity in skeletal muscle. AMPK is known to cause GLUT4 deployment to the plasma membrane, resulting in insulin-independent glucose uptake. The rare side effect, lactic acidosis, is thought to be caused by decreased liver uptake of serum lactate, one of the substrates of gluconeogenesis. In those with healthy renal function, the slight excess is simply cleared. However, those with severe renal impairment may accumulate clinically significant serum lactic acid levels. Other conditions that may precipitate lactic acidosis include severe hepatic disease and acute/decompensated heart failure.

Absorption: Absorbed over 6 hours, bioavailability is 50 to 60% under fasting conditions. Administration with food decreases and delays absorption. Some evidence indicates that the level of absorption is not dose-related, suggesting that absorption occurs through a saturable process. Limited data from animal and human cell cultures indicate that absorption occurs through a passive, non-saturable process, possibly involving a paracellular route. Peak action occurs 3 hours after oral administration.

Metabolism: Metformin is not metabolized.

Half Life: 6.2 hours. Duration of action is 8-12 hours.

Route of Elimination: Intravenous single-dose studies in normal subjects demonstrate that metformin is excreted unchanged in the urine and does not undergo hepatic metabolism (no metabolites have been identified in humans) nor biliary excretion. Approximately 90% of the drug is eliminated in 24 hours in those with healthy renal function. Renal clearance of metformin is approximately 3.5 times that of creatinine clearance, indicating the tubular secretion is the primary mode of metformin elimination.

Manufacturers: Ranbaxy pharmaceuticals inc, Andrx labs llc, Bristol myerssquibb co, Depomedinc, Actaviselizabethllc, Amneal pharmaceuticals nyllc, Apotexincetobicoke site, Barr laboratories inc, Impax laboratories inc, Ivax pharmaceuticals inc sub teva pharmaceuticals usa, Mutual pharmaceutical co inc, Mylan pharmaceuticals inc, Neurosciinc, Nostrum pharmaceuticals inc, Ranbaxy laboratories ltd, Sandoz inc, Sun pharmaceutical industries ltd, Teva pharmaceuticals usainc, Torrent pharmainc, Torrent pharmaceuticals ltd, Watson laboratories inc, Watson laboratories incflorida, Zydus pharmaceuticals usainc, Bristol myerssquibb co pharmaceutical research institute, Alphapharm party ltd, Alvogeninc, Apotexinc, Aurobindopharma ltd, Caraco pharmaceutical laboratories ltd, Drreddys laboratories inc, Genpharminc, Glenmark generics ltd, Granules india ltd, Indicuspharmallc, Ipca laboratories ltd, Mutual pharmacal co, Provident pharmaceutical inc, Watson laboratories FDA Approval: Metformin is an FDA approved drug.

CW231: (Table 1)

Name: ROSUVASTATIN

Drug Bank ID: DB01098 (APRD00546)

Type: small molecule
Group: Approved
Description: Rosuvastatin is an antilipemic agent that competitively inhibits hydroxymethylglutaryl-coenzyme A (HMG-CoA) reductase. HMG-CoA reducuase catalyzes the conversion of HMG-CoA to mevalonic acid, the rate-limiting step in cholesterol biosynthesis. Rosuvastatin belongs to a class of medications called statins and is used to reduce plasma cholesterol levels and prevent cardiovascular disease.

Brand Name: Astende, Cirantan, Cresadex, Crestor, Provisacor, Razel, Rosedex, Rosimol, Rosumed, Rosustatin Indication: Used as an adjunct to dietary therapy to treat primary hyperlipidemia (heterozygous familial and nonfamilial), mixed dyslipidemia and hypertriglyceridemia. Also indicated for homozygous familial hypercholesterolemia as an adjunct to other lipid-lowering therapies or when other such therapies are not available. Furthermore, it is used to slow the progression of atherosclerosis and for primary prevention of cardiovascular disease.

Pharmacodynamics: Rosuvastatin is a synthetic, enantiomerically pure antilipemic agent. It is used to lower total cholesterol, low density lipoprotein-cholesterol (LDL-C), apolipoprotein B (apoB), non-high density lipoprotein-cholesterol (non-HDL-C), and trigleride (TG) plasma concentrations while increasing HDL-C concentrations. High LDL-C, low HDL-C and high TG concentrations in the plasma are associated with increased risk of atherosclerosis and cardiovascular disease. The total cholesterol to HDL-C ratio is a strong predictor of coronary artery disease and high ratios are associated with higher risk of disease. Increased levels of HDL-C are associated with lower cardiovascular risk. By decreasing LDL-C and TG and increasing HDL-C, rosuvastatin reduces the risk of cardiovascular morbidity and mortality.

Mechanism of Action: Rosuvastatin is a competitive inhibitor of HMG-CoA reductase. HMG-CoA reductase catalyzes the conversion of HMG-CoA to mevalonate, an early rate-limiting step in cholesterol biosynthesis. Rosuvastatin acts primarily in the liver. Decreased hepatic cholesterol concentrations stimulate the upregulation of hepatic low density lipoprotein (LDL) receptors which increases hepatic uptake of LDL. Rosuvastatin also inhibits hepatic synthesis of very low density lipoprotein (VLDL). The overall effect is a decrease in plasma LDL and VLDL. In vitro and in vivo animal studies also demonstrate that rosuvastatin exerts vasculoprotective effects independent of its lipid-lowering properties. Rosuvastatin exerts an anti-inflammatory effect on rat mesenteric microvascular endothelium by attenuating leukocyte rolling, adherence and transmigration (PMID: 11375257). The drug also modulates nitric oxide synthase (NOS) expression and reduces ischemic-reperfusion injuries in rat hearts (PMID: 15914111). Rosuvastatin increases the bioavailability of nitric oxide (PMID: 11375257, 12031849, 15914111) by upregulating NOS (PMID: 12354446) and by increasing the stability of NOS through post-transcriptional polyadenylation (PMID: 17916773). It is unclear as to how rosuvastatin brings about these effects though they may be due to decreased concentrations of mevalonic acid.

Absorption: Bioavailability is approximately 20%. Peak plasma concentrations were reached 3 to 5 hours following oral dosing. Both Cmax and AUC increased in approximate proportion to CRESTOR dose. Food has no effect on the AUC of rosuvastatin.

Metabolism: Not extensively metabolized. Only ~10% is excreted as metabolite. Cytochrome P450 (CYP) 2C9 is primarily responsible for the formation of rosuvastatin's major metabolite, N-desmethylrosuvastatin. N-desmethylrosuvastatin has approximately 50% of the pharmacological activity of its parent compound in vitro. Rosuvastatin clearance is not dependent on metabolism by cytochrome P450 3A4 to a clinically significant extent. Rosuvastatin accounts for greater than 90% of the pharmacologic action. Inhibitors of CYP2C9 increase the AUC by less than 2-fold. This interaction does not appear to be clinically significant.

Half-life: 19 hours

Route of Elimination: Rosuvastatin is not extensively metabolized; approximately 10% of a radiolabeled dose is recovered as metabolite. Following oral administration, rosuvastatin and its metabolites are primarily excreted in the feces (90%). After an intravenous dose, approximately 28% of total body clearance was via the renal route, and 72% by the hepatic route.

Manufacturers: Ipr pharmaceuticals Inc

FDA Approval: Rosuvastatin is an FDA approved drug.

Cancer and Methods of Treatment

In an embodiment, the present disclosure provides a process for preparing a composition, wherein the composition comprises the compounds nelfinavir, metformin and rosuvastatin optionally along with a pharmaceutically-acceptable excipient, wherein the process comprises the step of combining the compounds and the optional excipient in any order thereof.

In an embodiment, the disclosure described herein provides therapeutic methods for the treatment of cancer.

In one embodiment of the present disclosure, the disclosure provides a method for treating a subject either suspected of having or having a condition or mutation or a combination thereof, wherein said condition is selected from a group comprising cancers where PI3K/AKT/mTOR signaling axis is highly activated such as tumors carrying aberration in PTEN gene, optionally along with aberration in P53 gene and related genes selected from group comprising PI3K, CDKN2A, MDM2 and MDM4, including lung cancer, colorectal cancer, pancreatic cancer, glioblastoma, multiple myeloma etc or any combination of conditions thereof, said method comprising act of administering to the subject a combination of—a) therapeutically-effective amount of Nelfinavir; b) Metformin; and c) Rosuvastatin and wherein the administration uses one or a plurality of dosage forms, each dosage form comprising one or more inhibitors, and wherein each dosage form optionally comprises a pharmaceutically-acceptable excipient.

In an embodiment, the disclosure provides a use of a combination of compounds in the preparation of a medicament for the treatment of cancer and associated conditions, wherein the compounds are: i. Nelfinavir; ii. Metformin; iii. Rosuvastatin; and optionally a pharmaceutically acceptable excipient.

In an embodiment of the present disclosure, pharmaceutical compositions containing compounds described herein can be administered for prophylactic and/or therapeutic treatments. In therapeutic applications, the compositions are administered to a subject already suffering from a disease or condition, in an amount sufficient to cure or at least partially arrest the symptoms of the disease or condition, or to cure, heal, improve, or ameliorate the condition itself. Amounts effective for this use can vary based on the severity and course of the disease or condition, previous therapy, the subject's health status, weight, and response to the drugs, and the judgment of the treating physician. Pharmaceutically-acceptable amounts can be determined by routine experimentation, for example, by a dose escalation clinical trial.

In an embodiment of the present disclosure, multiple therapeutic agents can be administered in any order or simultaneously. If simultaneously, the multiple therapeutic agents can be provided in a single, unified form, or in multiple forms, for example, as multiple separate pills. The compounds can be packed together or separately, in a single package or in a plurality of packages. One or all of the therapeutic agents can be given in multiple doses. If not simultaneous, the timing between the multiple doses may vary to as much as about a month.

In an embodiment, composition of the disclosure is administered sequentially at a time interval. The time interval can range from about 1 second to about 800 minutes.

In an embodiment, therapeutics are combined with genetic or genomic testing to determine whether that individual is a carrier of a mutant gene that is known to be correlated with certain diseases or conditions. A personalized medicine approach can be used to provide companion diagnostic tests to discover a subject's predisposition to certain conditions and susceptibility to therapy. For example, a subject who is an anti-EGFR non responder could be identified through companion diagnostics. The companion diagnostic test can be performed on a tumor biopsy.

In an embodiment, compounds/composition described herein can be administered before, during, or after the occurrence of a disease or condition, and the timing of administering the composition containing a compound can vary. For example, the compounds can be used as a prophylactic and can be administered continuously to subjects with a propensity to conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be through any route practical, such as by any route described herein using any formulation described herein. A compound can be administered as soon as is practicable after the onset of a disease or a condition is detected or suspected, and for a length of time necessary for the treatment of the disease, such as, for example, from about 1 month to about 3 months. The length of treatment can vary for each subject, and the length can be determined using the known criteria.

EXAMPLES

The present disclosure is further elucidated by the following illustrative, non-limiting examples.

Example 1

Virtual Tumor Based In-Vivo Aligned Studies

The composition of the disclosure are analyzed on a virtual tumor cell system designed to represent the disease state, and customized to match a specific molecular profile of specific cancer baselines. These experiments are validated by the experiment provided below:

The baselines selected for the virtual experiments include:
a) U251 human cell line harboring mutation in PTEN, TP53 and CDKN2A
b) U87 cell line harbouring mutation in PTEN and CDKN2A.
c) LN229 cell line harbouring mutation in TP53 and CDKN2A.

In these virtual experiments, the system is first triggered with the respective oncogenic mutations aligned to the specific profiles and then simulated for a minimum of about 35 hours simulation time. The simulation time is selected to allow the system to attain the severe oncogenic state through activation of autocrine and paracrine pathway loops affecting all oncogenic mediators like growth factors, kinases and transcription factors. After about 35 hours of simulation, a system customized to the above mentioned tumor profile is created.

The drug compounds Nelfinavir, Metformin and Rosuvastatin individually and in combination are administered concomitantly to the Virtual Tumor cell, and the system simulated again for a minimum of about 18-20 hours simulation time. The drug administration is performed at multiple dosage ratios across an array of samples for each drug. The effect of the multiple dosage ratios is evaluated after about 18-20 hours of simulation by assaying the extent of decrease/increase in the tumor cell survival, apoptosis and proliferation markers. The major markers assayed include active complexes of CDK4-CCND1, CDK2-CCNE, CDK2-CCNA and CDK1-CCNB1 responsible for cell proliferation. Other proteins including BCL2, BIRC5, BIRC2, BAX, CASP3 and PARP1 cleaved were assayed to determine their effect on tumor cell survival and apoptosis. Other vital biomarkers including VEGFA were assayed to estimate the levels of angiogenesis.

Based on the assayed biomarkers, an overall viability score was calculated as a ratio of survival/apoptosis.

"Viability" is a scale to measure change in tumorogenic symptoms. A reduction greater than 30% is considered as being moderately effective and a reduction greater than 50% is considered being an effective therapy.

Viability index is a ratio of cumulative measure of an average of survival over apoptotic markers. It is defined as a ratio of the cumulative survival index over the apoptosis index. The survival index comprises of AKT1, BCL2, BIRC5, BIRC2, MCL1 and XIAP, end point markers. The apoptosis index comprises of BAX, CASP3, PMAIP1, CASP8, and BCL2L11.

Proliferation index is a cumulative measure of an average of cell cycle checkpoint complexes comprising of CDK4-CCND1, CDK2-CCNE, CDK2-CCNA and CDK1-CCNB1 active complexes.

Figure 1B:
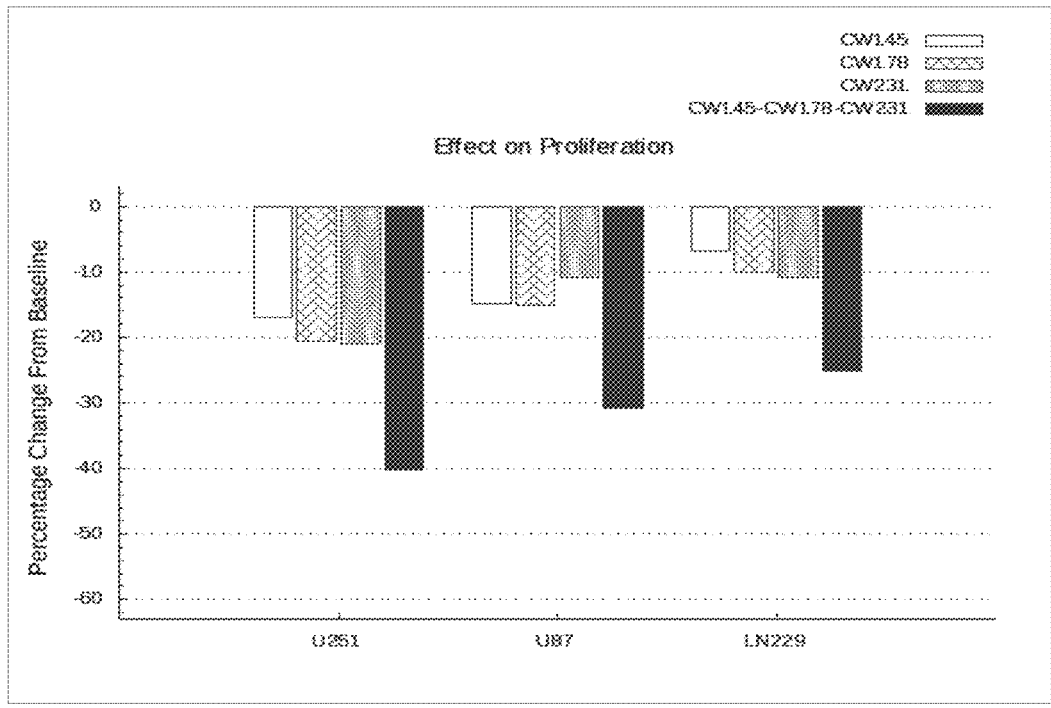
FIG. 1B depicts the impact of Single vs. Triple combination comprising of drugs CW145 (Nelfinavir), CW178 (Metformin) and CW231 (Rosuvastatin) at IC20 concentration on proliferation phenotype in U251 cell line (having mutation in PTEN, TP53 and CDKN2A), U87 cell line (having PTEN, CDKN2A mutation) and LN229 (having TP53, CDKN2A mutation).
Figure 1C:
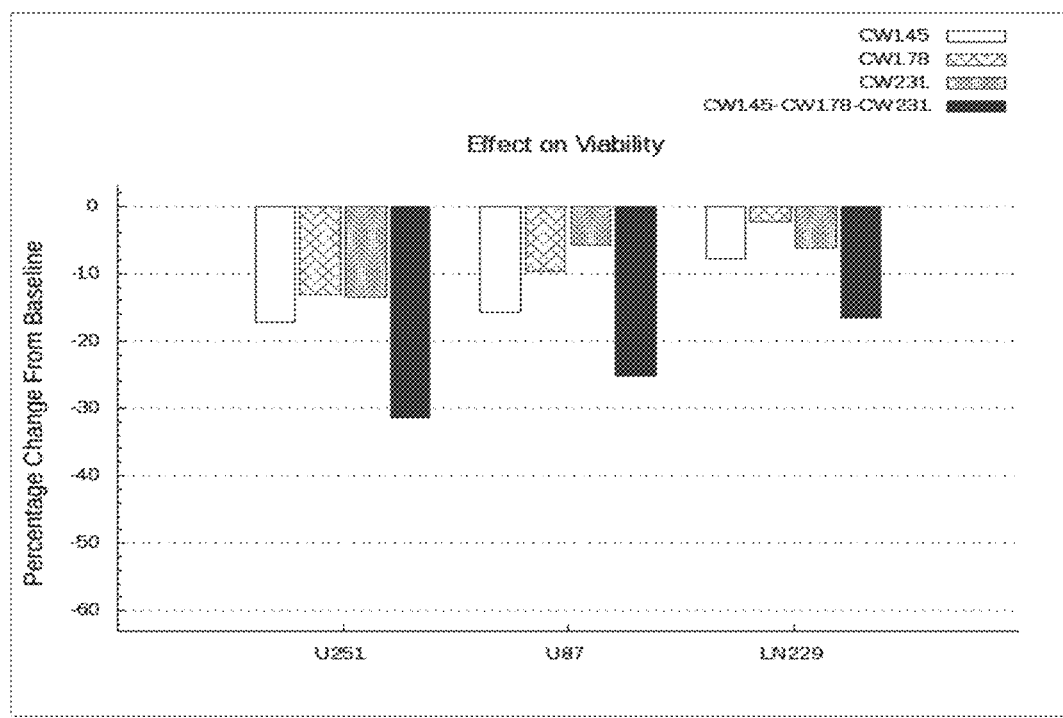
FIG. 1C depicts the impact of Single vs. Triple combination comprising of drugs CW145 (Nelfinavir), CW178 (Metformin) and CW231 (Rosuvastatin) at IC20 concentration on viability phenotype in U251 cell line (having mutation in PTEN, TP53 and CDKN2A), U87 cell line (having PTEN, CDKN2A mutation) and LN229 (having TP53, CDKN2A mutation).
Figure 2A:
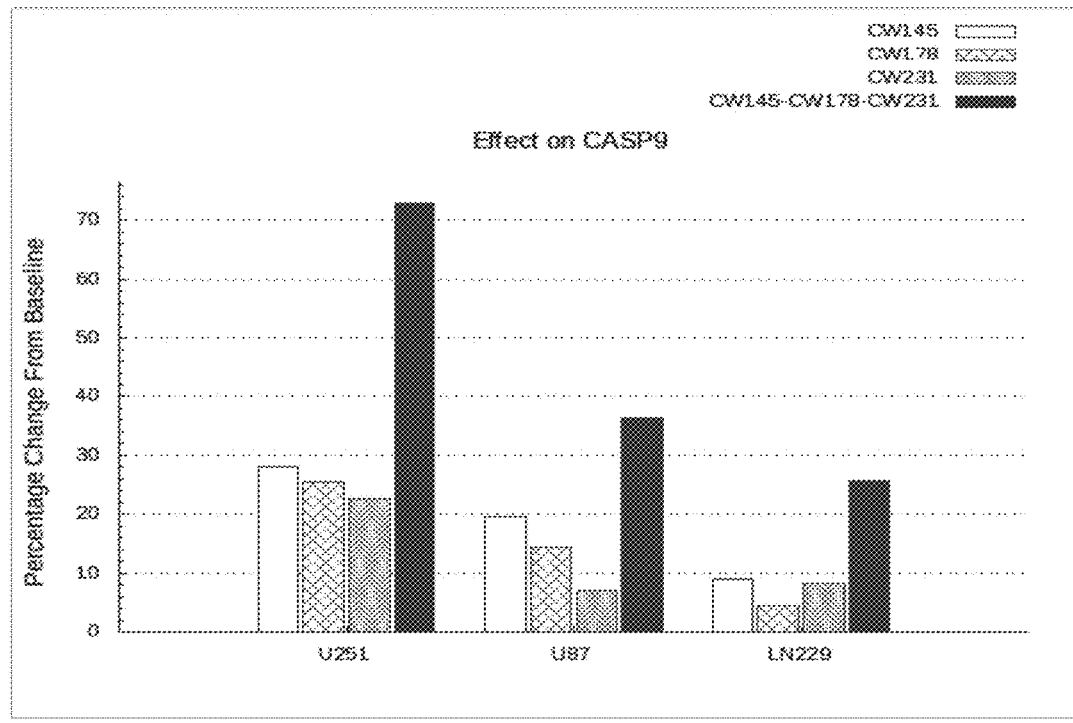
FIG. 2A depicts the impact of Single vs. Triple combination comprising of drugs CW145 (Nelfinavir), CW178 (Metformin) and CW231 (Rosuvastatin) at IC20 concentration on CASP3 in U251 cell line (having mutation in PTEN, TP53 and CDKN2A), U87 cell line (having PTEN, CDKN2A mutation) and LN229 (having TP53, CDKN2A mutation).
Figure 2B:
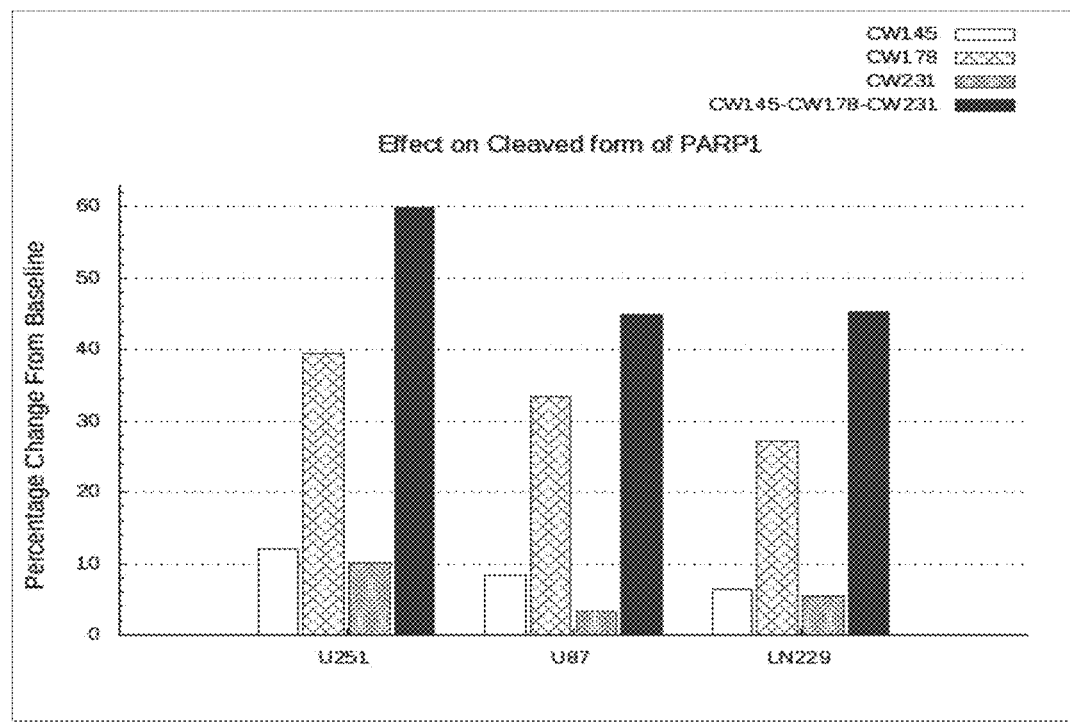
FIG. 2B depicts the impact of Single vs. Triple combination comprising of drugs CW145 (Nelfinavir), CW178 (Metformin) and CW231 (Rosuvastatin) at IC20 concentration on PARP1 Cleaved in U251 cell line (having mutation in PTEN, TP53 and CDKN2A), U87 cell line (having PTEN, CDKN2A mutation) and LN229 (having TP53, CDKN2A mutation).
Figure 2C:
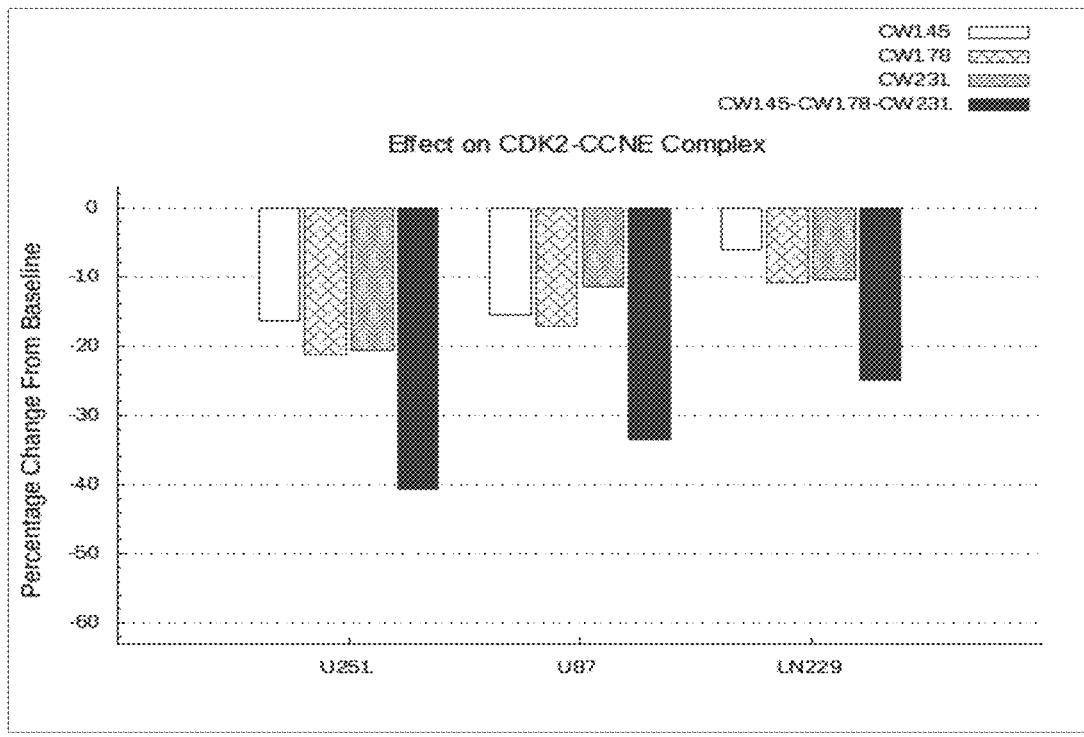
FIG. 2C depicts the impact of Single vs. Triple combination comprising of drugs CW145 (Nelfinavir), CW178 (Metformin) and CW231 (Rosuvastatin) at IC20 concentration on CDK2-CCNE complex in U251 cell line (having mutation in PTEN, TP53 and CDKN2A), U87 cell line (having PTEN, CDKN2A mutation) and LN229 (having TP53, CDKN2A mutation).
Figure 2D:
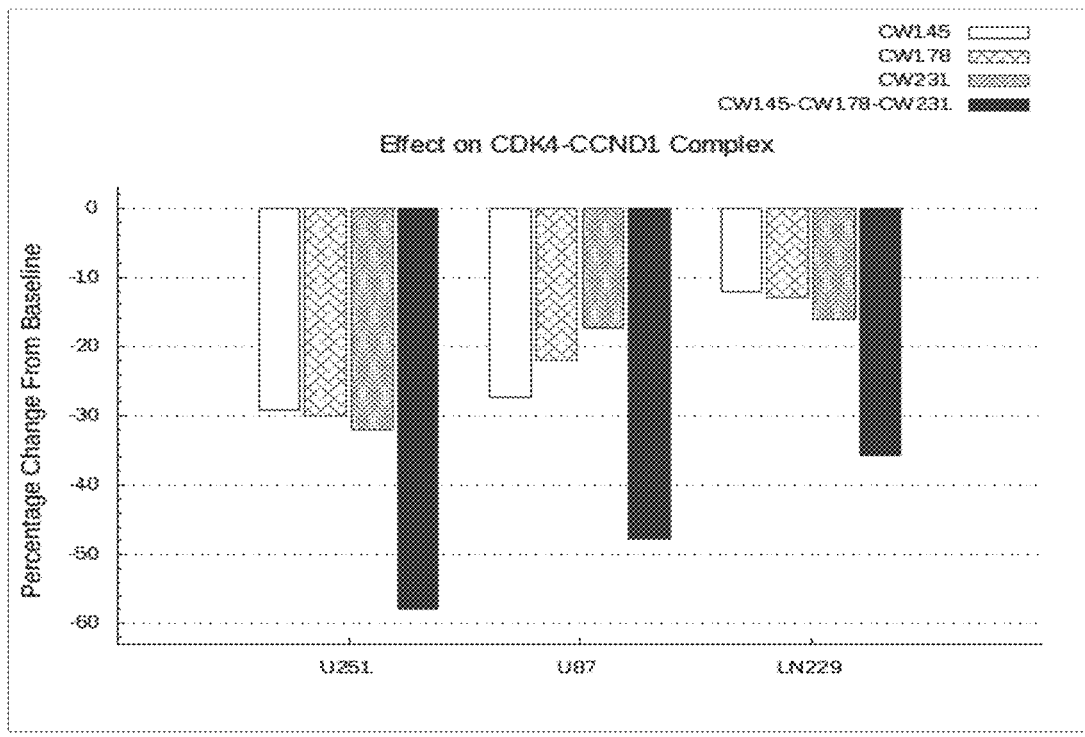
FIG. 2D depicts the impact of Single vs. Triple combination comprising of drugs CW145 (Nelfinavir), CW178 (Metformin) and CW231 (Rosuvastatin) at IC20 concentration on CDK4-CCND1 complex in U251 cell line (having mutation in PTEN, TP53 and CDKN2A), U87 cell line (having PTEN, CDKN2A mutation) and LN229 (having TP53, CDKN2A mutation).
Figure 2E:
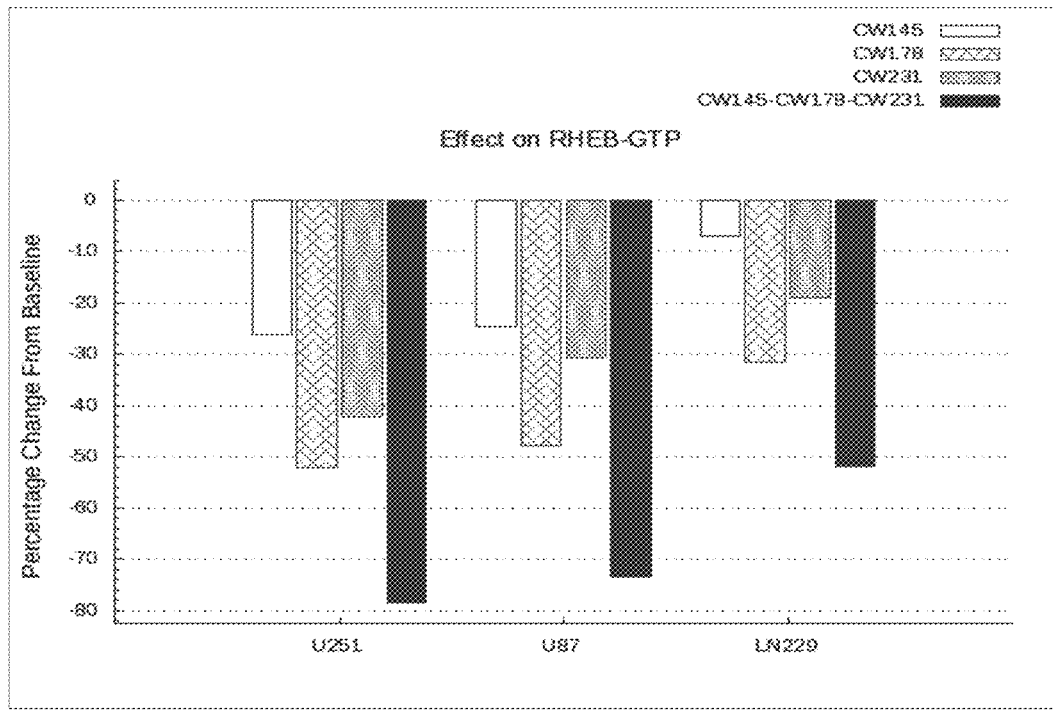
FIG. 2E depicts the impact of Single vs. Triple combination comprising of drugs CW145 (Nelfinavir), CW178 (Metformin) and CW231 (Rosuvastatin) at IC20 concentration on RHEB-GTP in U251 cell line (having mutation in PTEN, TP53 and CDKN2A), U87 cell line (having PTEN, CDKN2A mutation) and LN229 (having TP53, CDKN2A mutation).
Figure 2F:
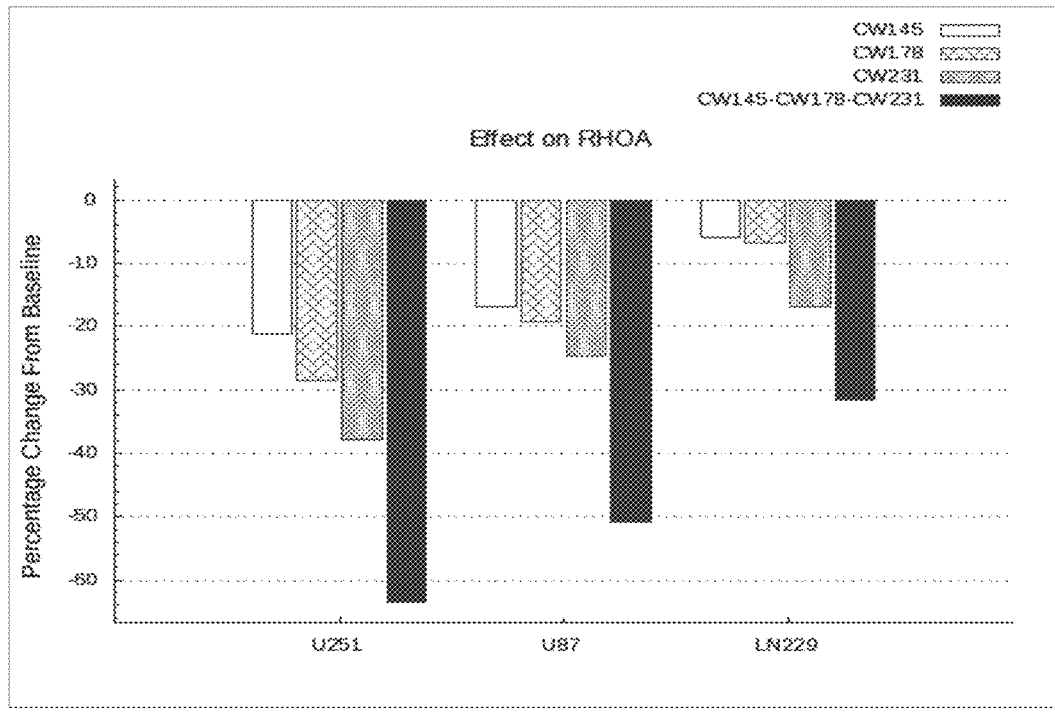
FIG. 2F depicts the impact of Single vs. Triple combination comprising of drugs CW145 (Nelfinavir), CW178 (Metformin) and CW231 (Rosuvastatin) at IC20 concentration on RHOA in U251 cell line (having mutation in PTEN, TP53 and CDKN2A), U87 cell line (having PTEN, CDKN2A mutation) and LN229 (having TP53, CDKN2A mutation).

FIGS. 1 A-C illustrates the impact of combination of drugs (composition) versus single drugs, on U251 cell line (having mutation in PTEN, TP53 and CDKN2A), U87 cell line (having PTEN, CDKN2A mutation) and LN229 (having TP53, CDKN2A mutation) with respect to relative growth phenotype, proliferation phenotype and viability phenotype. Here the concentration of each drug is at IC20. IC20 is the concentration of drug that causes 20% reduction in relative growth (IC20).

FIGS. 2 A-F illustrates the impact of combination of drugs (composition) versus single drugs on U251 cell line (having mutation in PTEN, TP53 and CDKN2A), U87 cell line (having PTEN, CDKN2A mutation) and LN229 (having TP53, CDKN2A mutation), with respect to the biomarker levels (CASP3, PARP1 Cleaved, CDK2-CCNE, CDK4-CCND1, RHEB-GTP and RHOA).

Figure 3:
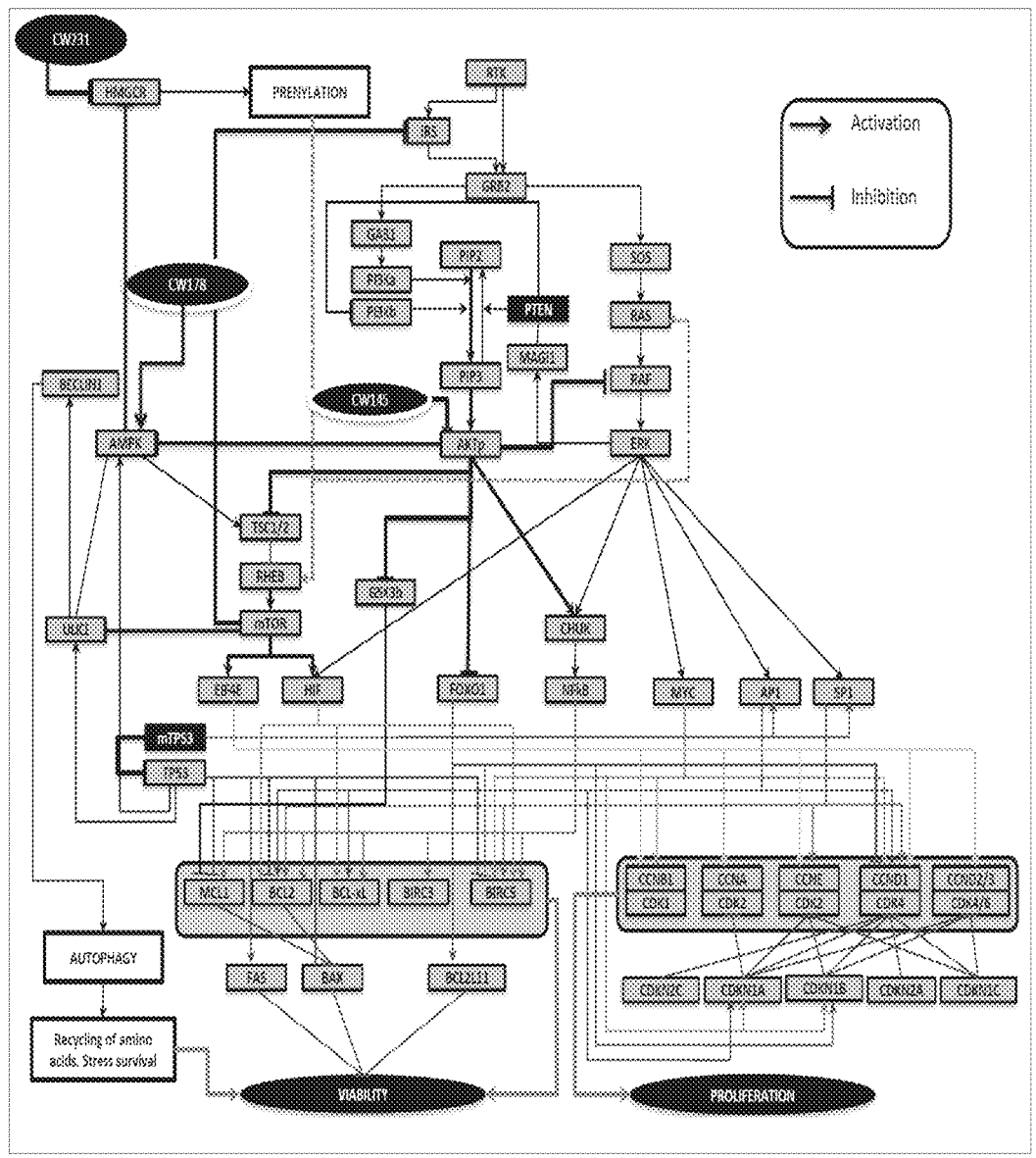
FIG. 3 depicts scientific rationale for the combination (Nelfinavir+ Metformin+ Rosuvastatin) of the present disclosure.

FIG. 3 illustrates scientific rationale for the combination therapy and its impact on the key phenotypes of PTEN driven cancer.

Example 2

Bar Plot Illustrating the Effect of Nelfinavir, Metformin and Rosuvastatin Alone and in Combination in U251, U87 and LN229 Cell Lines In-Vitro.

TABLE 2

| Fields | Details |
|---|---|
| Experimental Protocol | The three drugs CW145-Nelfinavir, CW178-Metformin and CW231-Rosuvastatin are tested in combination at varying dosages on the following cell lines in-vitro:<br>1. PTEN, TP53 and CDKN2A mutated cell line-U251,<br>2. PTEN and CDKN2A mutated cell line-U87<br>3. TP53 and CDKN2A mutated cell line-LN229. |

U251 cell line is procured from Sigma-Aldrich (Catalog number: 09063001). The U87 human cell line is procured from ATCC (American Type Culture Collection, Manassas, Va., ATCC® HTB-14™). LN229 cell line is procured from ATCC (American Type Culture Collection, Manassas, Va., ATCC® CRL2611™). The cells are resuspended in a media containing 10% FBS (Gibco lot#1259720) and 4× Gentamicin followed by transferring about 100 µl to each well in an assay plate (5000 cells/well; passage#2). DMSO, Digitoxin and drugs (Nelfinavir, Metformin and Rosuvastatin individually and in combination) are serial diluted in an assay media. 100 µl/well of the diluted sample is added to assay plate containing resuspended cells. Final assay volume of each well is about 200 µl, containing 10% FBS, 2× Gentamicin, DMSO, Digitoxin and drugs. The assay plate is incubated for about 71 hours followed by addition of about 20 µl of Promega Substrate CellTiter 96 Aqueous One Solution Reagent to each well. It is incubated at 37° C. The absorbance of the sample is read at about 490 nm.

Results:

FIGS. 4 A-C depicts the impact of Single vs. Triple combination comprising of drugs CW145 (Nelfinavir), CW178 (Metformin) and CW231 (Rosuvastatin) on U251 cell line (having mutation in PTEN, TP53 and CDKN2A), U87 cell line (having PTEN, CDKN2A mutation) and LN229 (having TP53, CDKN2A mutation) with respect to percent relative growth.

Figure 4A:
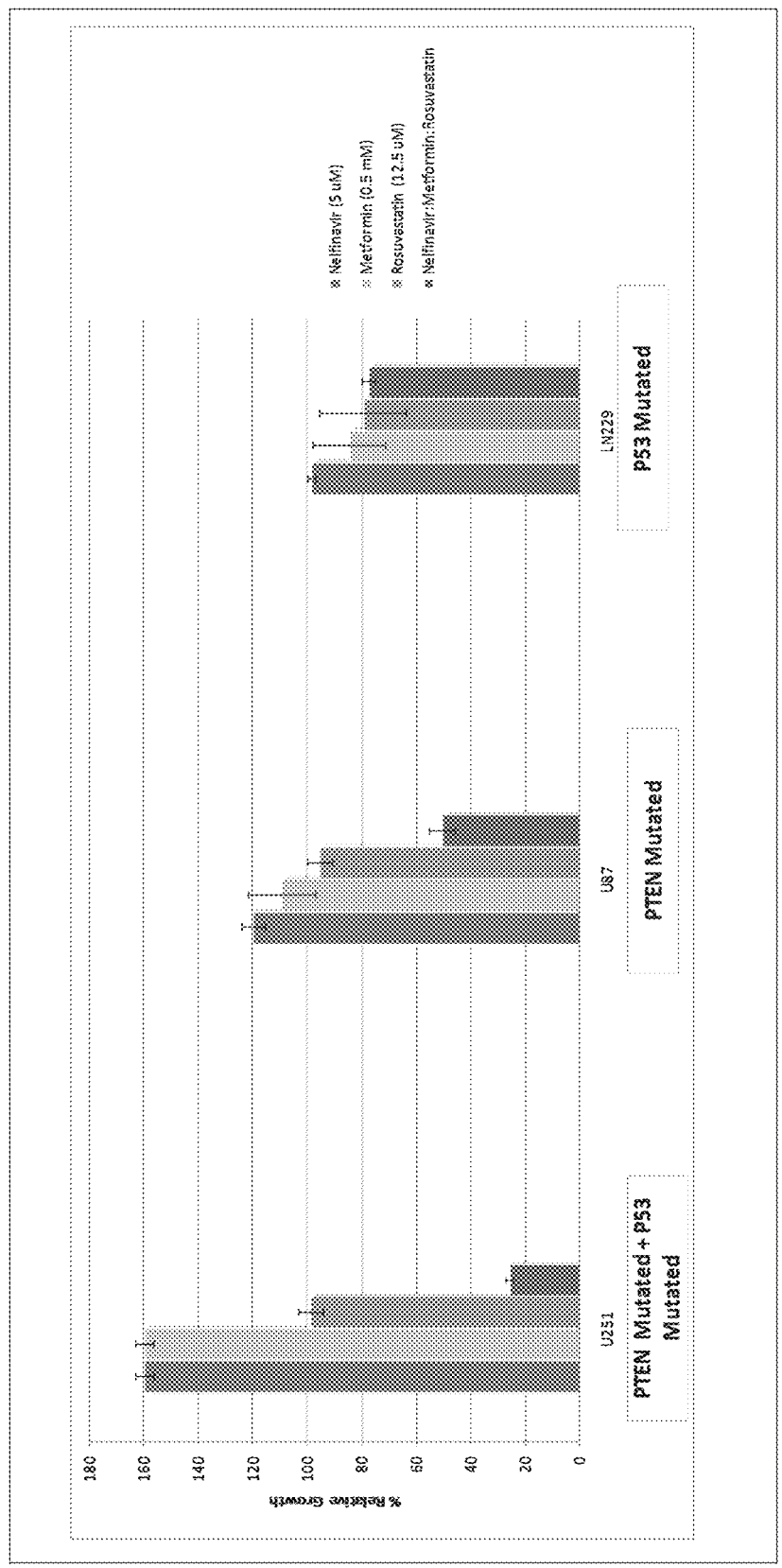
FIGS. 4A, 4B and 4C depicts the percentage of relative growth in-vitro in U251 cell line (having mutation in PTEN, TP53 and CDKN2A), U87 cell line (having PTEN, CDKN2A mutation) and LN229 (having TP53, CDKN2A mutation) upon treatment with the composition comprising Nelfinavir, Metformin and Rosuvastatin and in comparison with individual drugs in each of the three cell lines.
Figure 4B:
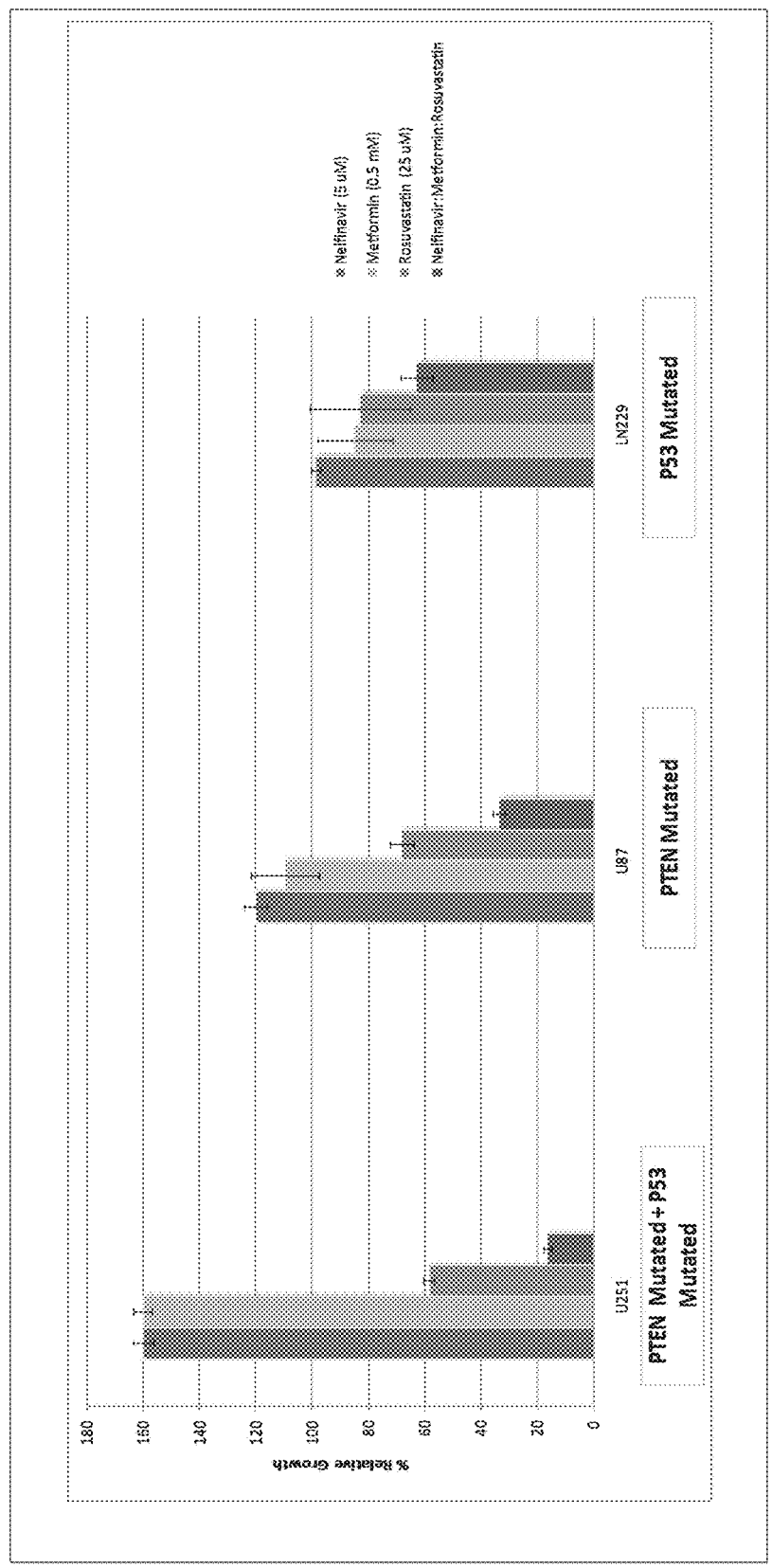
Figure 4C:
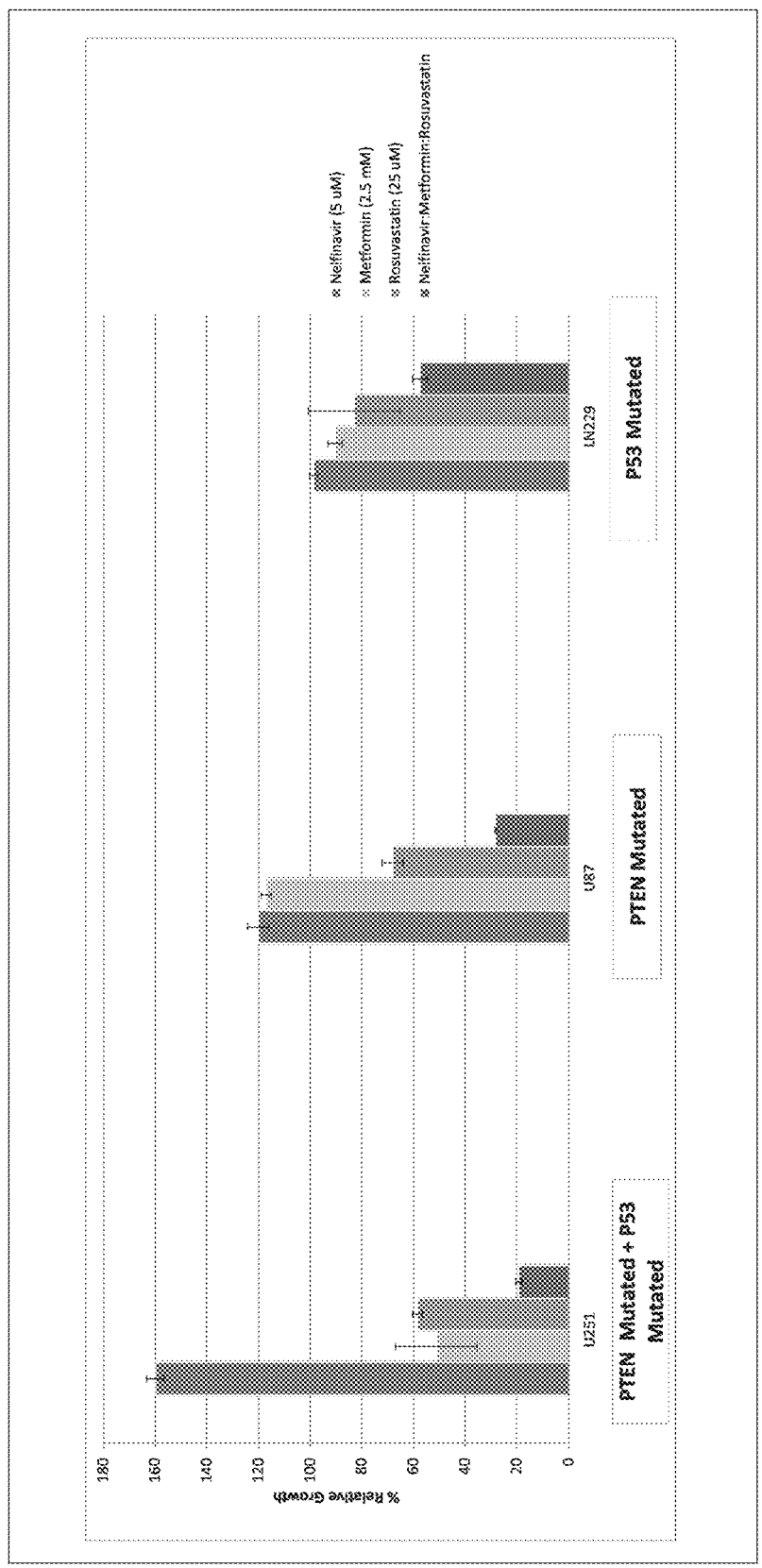

FIGS. 4A, 4B and 4C illustrate the concentrations of drugs individually and the three drug combinations on the x-axis and percentage change in relative growth on the y-axis. The individual concentrations of the drugs—Nelfinavir, Metformin and Rosuvastatin as indicated in FIG. 4A are 5 µM, 0.5 mM and 12.5 µM respectively. At these concentrations, the individual drugs do not show much efficacy (with regard to reduction in relative growth) in the three cell lines. However, when a composition comprising a combination of Nelfinavir, Metformin and Rosuvastatin, at concentrations of 5 µM, 0.5 mM and 12.51 µM respectively, are combined and employed over the three cell lines, a significant reduction in relative growth (as compared to the individual drugs) is observed in U251 cell line (which harbours mutation in PTEN as well as TP53, CDKN2A) indicating synergistic effect of the composition in cancer profiles characterized by PTEN and TP53 mutation.

The said composition also shows considerable reduction (as compared to the individual drugs) in relative growth in U87 cell line (which harbours PTEN mutation along with CDKN2A mutation) indicating synergistic effect of the composition in cancer profiles characterized by PTEN mutation. However, it is observed that the composition is not very efficacious on LN229 cell line (which harbours TP53 mutation along with CDKN2A mutation), although a small percentage of reduction in relative growth is seen (when compared to the individual drugs), thereby indicating that the composition comprising nelfinavir, metformin and rosuvastatin is the most efficacious in treating cancers characterized by aberration in PTEN, optionally along with aberration in TP53 gene.

The FIGS. 4B and 4C also show similar results for the composition over the three cell lines: U251, U87 and LN229, wherein the components Nelfinavir, Metformin and Rosuvastatin are taken at concentrations of 5 µM, 0.5 mM, 25 µM and 5 µM, 2.5 mM, 25 µM respectively.

In other words, the composition comprising Nelfinavir, Metformin and Rosuvastatin is the most efficacious in the treatment of cancer characterized by aberration in PTEN gene optionally along with aberration in TP53 gene.

CONCLUSION

From the above experimental results in U251, U87 and LN229 cell lines, it is evident that the three drug combination of Nelfinavir, Metformin and Rosuvastatin is effective in reducing the cell survival. Further, the said three drug combination is the most effective in the treatment of cancers caused due to aberration in PTEN gene optionally along with aberration in TP53 gene.

We claim:

1. A method for treating cancer caused by an aberration in PTEN gene, optionally along with an aberration in TP53 gene in a subject in need or want of relief thereof, the method comprising administering to the subject a composition comprising Nelfinavir, Metformin, and Rosuvastatin optionally along with a pharmaceutically acceptable excipient.

2. The method as claimed in claim 1, wherein the aberration in PTEN gene is optionally associated with an aberration in PI3K gene.

3. The method as claimed in claim 1, wherein the aberration in TP53 gene is associated with an aberration in genes selected from the group comprising CDKN2A, MDM2, MDM4, and combinations thereof.

4. The method as claimed in claim 1, wherein the pharmaceutically acceptable excipient is selected from the group comprising granulating agents, binding agents, lubricating agents, disintegrating agents, sweetening agents, glidants, anti-adherents, anti-static agents, surfactants, anti-oxidants, gums, coloring agents, flavouring agents, coating agents, plasticizers, preservatives, suspending agents, emulsifying agents, plant cellulosic material, spheronization agents, and any combination thereof.

5. A method of inhibiting cancer cells/inducing cytotoxicity in cancer cells/modulating markers in cancer cells, wherein cancer is caused by aberration in PTEN gene, optionally along with aberration in TP53 gene, said method comprising an act of contacting the cancer cells with a composition comprising Nelfinavir, Metformin and Rosuvastatin optionally along with a pharmaceutically acceptable excipient.

6. The method as claimed in claim 5, wherein the aberration in PTEN gene is optionally associated with aberration in PI3K gene.

7. The method as claimed in claim 5, wherein the aberration in TP53 gene is associated with aberration in genes selected from a group comprising CDKN2A, MDM2, MDM4 and combinations thereof.

* * * * *